(12) United States Patent
Ebright et al.

(10) Patent No.: US 8,372,839 B2
(45) Date of Patent: Feb. 12, 2013

(54) BIPARTITE INHIBITORS OF BACTERIAL RNA POLYMERASE

(75) Inventors: Richard H. Ebright, North Brunswick, NJ (US); Dongye Wang, Edison, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 1149 days.

(21) Appl. No.: 12/084,018

(22) PCT Filed: Nov. 4, 2006

(86) PCT No.: PCT/US2006/043152
§ 371 (c)(1), (2), (4) Date: Aug. 11, 2008

(87) PCT Pub. No.: WO2007/089310
PCT Pub. Date: Aug. 9, 2007

(65) Prior Publication Data
US 2009/0137467 A1   May 28, 2009

Related U.S. Application Data

(60) Provisional application No. 60/733,200, filed on Nov. 4, 2005.

(51) Int. Cl.
*A61K 31/497* (2006.01)
*A01N 43/54* (2006.01)
*C07D 239/70* (2006.01)
(52) U.S. Cl. .................. 514/252.1; 514/258.1; 544/253
(58) Field of Classification Search ............... 514/252.1, 514/258.1; 544/253
See application file for complete search history.

(56) References Cited

U.S. PATENT DOCUMENTS

| | | |
|---|---|---|
| 5,556,949 A | 9/1996 | Ebright et al. |
| 6,919,333 B2 | 7/2005 | Ebright et al. |
| 7,141,655 B2 | 11/2006 | Ebright et al. |
| 7,282,373 B2 | 10/2007 | Ebright et al. |
| 7,371,745 B2 | 5/2008 | Ebright et al. |
| 7,381,572 B2 | 6/2008 | Ebright et al. |
| 2002/0090613 A1 | 7/2002 | Seul et al. |
| 2005/0059063 A1 | 3/2005 | Seul et al. |
| 2006/0127905 A1 | 6/2006 | Ebright |
| 2006/0160158 A1 | 7/2006 | Ebright |
| 2006/0246479 A1 | 11/2006 | Ebright |
| 2007/0196886 A1 | 8/2007 | Ebright et al. |

FOREIGN PATENT DOCUMENTS

WO   WO2005/024040   3/2005

OTHER PUBLICATIONS

Gnatt et al., "Structural Basis of Transcription: An RNA Polymerase II Elongation Complex at 3.3 A Resolution", Science, Jun. 8, 2001, vol. 292, pp. 1876-1882.

*Primary Examiner* — Paul V. Ward
(74) *Attorney, Agent, or Firm* — Davidson, Davidson & Kappel, LLC

(57) ABSTRACT

The invention provides a compound having a structural formula (I): X-α-Y, wherein X is an moiety that binds to the Rif pocket of a bacterial RNA polymerase, Y is a moiety that binds to the secondary channel of a bacterial RNA polymerase, and α is a linker. The compound can act as an inhibitor of bacterial RNA polymerase. The invention has applications in control of bacterial gene expression, control of bacterial growth, antibacterial chemistry, and antibacterial therapy.

42 Claims, 9 Drawing Sheets

● {rifamycin SV}-CH2C(O)NH(CH2)nNHC(O)CH3 (n=12)
○ rifamicrocin 1-6 IC50=130 nM
▼ rifamicrocin 1-8 IC50=102 nM
▽ rifamicrocin 1-10 IC50=95 nM
■ rifamicrocin 1-12 IC50=48 nM
◆ rifamycin B IC50=420 nM ▲ {rifamycin SV}-CH2C(O)NH(CH2)nNHC(O)CH2CH2CCH
△ rifamicrocin 2-10 IC50 = 220 nM
● rifamycin B IC50 = 420 nM

BIPARTITE INHIBITORS OF BACTERIAL RNA POLYMERASE

CROSS-REFERENCE TO RELATED APPLICATIONS

This application claims priority to U.S. Provisional Application Ser. No. 60/733,200 filed Nov. 4, 2005, the contents of which are incorporated herein by reference.

GOVERNMENT SUPPORT

This invention was supported with U.S. Government funds (NIH RO1-GM41376). Therefore, the Government may have rights in the invention.

BACKGROUND ART

Bacterial infections remain among the most common and deadly causes of human disease. Infectious diseases are the third leading cause of death in the United States and the leading cause of death worldwide (Binder et al. (1999) Science 284, 1311-1313). Multi-drug-resistant bacteria now cause infections that pose a grave and growing threat to public health. It has been shown that bacterial pathogens can acquire resistance to first-line and even second-line antibiotics (Stuart B. Levy, The Challenge of Antibiotic Resistance, in Scientific American, 46-53 (March, 1998); Walsh, C. (2000) Nature 406, 775-781; Schluger, N. (2000) Int. J. Tuberculosis Lung Disease 4, S71-S75; Raviglione et al., (2001) Ann. NY Acad. Sci. 953, 88-97). New approaches to drug development are necessary to combat the ever-increasing number of antibiotic-resistant pathogens.

RNA polymerase (RNAP) is the molecular machine responsible for transcription and is the target, directly or indirectly, of most regulation of gene expression (Ebright, R. (2000) J. Mol. Biol. 304, 687-698; Darst, S. (2001) Curr. Opin. Structl. Biol 11, 155-162; Cramer, P. (2002) Curr. Opin. Structl. Biol. 12, 89-97; Murakami & Darst (2003) Curr. Opin. Structl. Biol. 13, 31-39; Borukhov & Nudler (2003) Curr. Opin. Microbiol. 6, 93-100; Landick, R. (2001) Cell 105, 567-570; Korzheva & Mustaev (2001) Curr. Opin. Microbiol. 4, 119-125; Armache, et al. (2005) Curr. Opin. Structl. Biol. 15, 197-203; Woychik & Hampsey (2002); Cell 108, 453-463; Asturias, F. (2004) Curr. Opin. Genet Dev. 14, 121-129; Cramer, P. (2004) Curr. Opin. Genet. Dev. 14, 218-226; Geiduschek & Kassayetis (2001) J. Mol. Biol. 310, 1-26). Bacterial RNAP core enzyme has a molecular mass of ~380,000 Da and consists of one $\beta'$ subunit, one $\beta$ subunit, two $\alpha$ subunits, and one $\omega$ subunit; bacterial RNAP holoenzyme has a molecular mass of ~450,000 Da and consists of bacterial RNAP core enzyme in complex with the transcription initiation factor $\sigma$ (Ebright, R. (2000) J. Mol. Biol. 304, 687-698; Darst, S. (2001) Curr. Opin. Structl. Biol 11, 155-162; Cramer, P. (2002) Curr. Opin. Structl. Biol. 12, 89-97; Murakami & Darst (2003) Curr. Opin. Structl. Biol. 13, 31-39; Borukhov & Nudler (2003) Curr. Opin. Microbiol. 6, 93-100). Bacterial RNAP core subunit sequences are conserved across Gram-positive and Gram-negative bacterial species (Ebright, R. (2000) J. Mol. Biol. 304, 687-698; Darst, S. (2001) Curr. Opin. Structl. Biol. 11, 155-162; Iyer, et al. (2004) Gene 335, 73-88). Eukaryotic RNAP I, RNAP II, and RNAP III contain counterparts of all bacterial RNAP core subunits, but eukaryotic-subunit sequences and bacterial-subunit sequences exhibit only limited conservation (Ebright, R. (2000) J. Mol. Biol. 304, 687-698; Darst, S. (2001) Curr. Opin. Structl. Biol. 11, 155-162; Cramer, P. (2002) Curr. Opin. Structl Biol. 12, 89-97).

Recently, crystallographic structures have been determined for bacterial RNAP and eukaryotic RNAP II (Zhang et al., (1999) Cell 98, 811-824; Cramer et al., (2000) Science 288, 640-649; Nalyshkin et al., (2000) Cell 101, 601-611; Kim et al., (2000) Science 288, 1418-1421; Korzheva et al., (2000) Science 289, 619-625; Ebright, R. (2000) J. Mol. Biol. 304, 687-689; Cramer et al., (2001) Science 292, 1863-1876; Gnatt et al., (2001) Science 292, 1876-1882; Mekler et al., (2002) Cell 108, 599-614; Murakami et al., (2002) Science 296, 1280-1284; Murakami et al., (2002) Science 296, 1285-1290; Vassylyev et al., (2002) Nature 417, 712-719; Bushnell et al., (2004) Science 303, 983-988; Westover et al., (2004) Science 303, 1014-1016; Armache, et al., (2003) Proc. Natl. Acad. Sci. USA 100, 6964-6968). Moreover, cryo-EM structures have been determined for bacterial RNAP and eukaryotic RNAP I (Opalka, et al. (2000) Proc. Natl. Acad. Sci. USA 97, 617-622; Darst, et al. (2002) Proc. Natl. Acad. Sci. USA 99, 4296-4301; DeCarlo, et al. (2003) J. Mol. Biol. 329, 891-902).

Structures also have been determined for RNAP complexes with nucleic acids, nucleotides and inhibitors (Campbell, et al. (2001) Cell 104, 901-912; Artsimovitch, et al. (2005) Cell 122, 351-363; Campbell, et al. (2005) EMBO J. 24, 674-682; Artsimovitch, et al. (2004) Cell 117, 299-310; Tuske, et al. (2005) Cell 122, 541-522; Temiaov, et al. (2005) Mol. Cell 19, 655-666; Vassylyev, et al. (2005) Nature Structl. Biol. 12, 1086-1093; Gnatt, et al. (2001) Science 292, 1876-1882; Westover, et al. (2004a) Science 303, 1014-1016; Westover, et al. (2004b) Cell 119, 481-489; Ketenberger, et al. (2004) Mol. Cell 16, 955-965; Bushnell, et al. (2002) Proc. Natl. Acad. Sci. U.S.A. 99, 1218-1222; Kettenberger, et al. (2005) Natl. Structl. Mol. Biol. 13, 44-48).

The structures reveal that RNAP-bacterial or eukaryotic- has a shape reminiscent of a crab claw. The two "pincers" of the "claw" define the active-center cleft that can accommodate a double-stranded nucleic acid—and which has the active-center $Mg^{2+}$ at its base. The largest subunit ($\beta'$ in bacterial RNAP) makes up one pincer, termed the "clamp," and part of the base of the active-center cleft. The second-largest subunit ($\beta$ in bacterial RNAP) makes up the other pincer and part of the base of the active-center cleft.

Based on recent crystallographic structures for bacterial RNAP and eukaryotic RNAP II, biophysical results, and biochemical results, models have been proposed for the structures of transcription initiation and elongation complexes (Gnatt et al., (2001) Science 292, 1876-1882; Ebright, R. (2000) J. Mol. Biol. 304, 687-689; Naryshkin et al., (2000 Cell 101, 601-611; Kim et al., (2000) Science 288, 1418-1421; Korzheva et al., (2000) Science 289, 619-625; and Mekler et al., (2002) Cell 108:599-614). The models propose that nucleic acids completely fill the active-center cleft of RNAP, such that the only route by which incoming nucleoside triphosphate substrates (NTPs) can access the active center is through an approximately 25 Å long, 10 Å wide tunnel known as the "secondary channel" or "pore," that bores through the floor of the active-center cleft of RNAP opposite the active-center cleft. (Gnatt et al., (2001 Science 292, 1876-1882; Ebright, R. (2000) J. Mol. Biol. 304, 687-689

Bacterial RNAP is a proven target for antibacterial therapy (Chopra, et al. (2002) J. Appl. Microbiol. 92, 4S-15S; Darst, S. (2004) Trends Biochem. Sci. 29, 159-162). The suitability of bacterial RNAP as a target for antibacterial therapy follows from the fact that bacterial RNAP is an essential enzyme (permitting efficacy), the fact that bacterial RNAP subunit sequences are conserved (providing a basis for broad-spectrum activity), and the fact that bacterial RNAP subunit sequences are only weakly conserved in eukaryotic RNAP I, RNAP II, and RNAP III (providing a basis for therapeutic selectivity).

The rifamycin antibacterial agents—notably rifampicin, rifapentine, and rifabutin—function by binding to and inhibiting bacterial RNAP (Chopra, et al. (2002) *J. Appl Microbiol* 92, 4S-15S; Darst, S. (2004) *Trends Biochem. Sci.* 29, 159-162; Floss & Yu (2005) *Chem. Rev.* 105, 621-632; Campbell, et al. (2001) *Cell* 104, 901-912; Artsimovitch, et al. (2005) *Cell* 122, 351-363). The rifamycins bind to a site on bacterial RNAP adjacent to the RNAP active center and sterically and/or allosterically prevent extension of RNA chains beyond a length of 2-3 nt (Chopra, et al. (2002) *J. Appl Microbiol.* 92, 4S-15S; Darst, S. (2004) *Trends Biochem. Sci.* 29, 159-162; Floss & Yu (2005) *Chem. Rev.* 105, 621-632; Campbell, et al. (2001) *Cell* 104, 901-912; Artsimovitch, et al. (2005) *Cell* 122, 351-363).

The rifamycins are in current clinical use in treatment of Gram-positive and Gram-negative bacterial infections (Chopra, et al. (2002) *J. Appl. Microbiol.* 92, 4S-15S; Darst, S. (2004) *Trends Biochem. Sci.* 29, 159-162; Floss & Yu (2005) *Chem. Rev.* 105, 621-632; Campbell, et al. (2001) *Cell* 104, 901-912; Artsimovitch, et al. (2005) *Cell* 122, 351-363). The rifamycins are of particular importance in treatment of tuberculosis; the rifamycins are first-line anti-tuberculosis agents and are the only anti-tuberculosis agents able rapidly to clear infection and prevent relapse (Mitchison, D. (2000) *Int. J. Tuberc. Lung Dis.* 4, 796-806). The rifamycins also are of importance in treatment of bacterial infections relevant to biowarfare or bioterrorism; combination therapy with ciprofloxacin, clindamycin, and rifampicin was successful in treatment of inhalational anthrax following the 2001 anthrax attacks (Mayer, et al. (2001) *JAMA* 286, 2549-2553), and combination therapy with ciprofloxacin and rifampicin, or doxycycline with rifampicin, is recommended for treatment of future cases of inhalational anthrax (Centers for Disease Control and Prevention (2001) *JAMA* 286, 2226-2232).

The clinical utility of the rifamycin antibacterial agents is threatened by the existence of bacterial strains resistant to known rifamycins (Chopra, et al. (2002) *J. Appl. Microbiol.* 92, 4S-15S; Darst, S. (2004) *Trends Biochem. Sci.* 29, 159-162; Floss & Yu (2005) *Chem. Rev.* 105, 621-632; Campbell, et al. (2001) *Cell* 104, 901-912; Artsimovitch, et al. (2005) *Cell* 122, 351-363). Resistance to rifamycins typically involves substitution of residues in or immediately adjacent to the rifamycin binding site on bacterial RNAP—i.e., substitutions that directly decrease binding or function of rifamycins. A significant and increasing percentage of cases of tuberculosis are resistant to rifampicin (1.4% of new cases, 8.7% of previously treated cases, and 100% of cases designated multidrug-resistant, in 1999-2002; Schluger, N. (2000) *Int. J. Tuberc. Lung Dis.* 4, S71-S75; Raviglione, et al. (2001) *Ann. N.Y. Acad. Sci.* 953, 88-97; Zumia, et al. (2001) *Lancet Infect. Dis.* 1, 199-202; Dye, et al. (2002) *J. Infect. Dis.* 185, 1197-1202; WHO/IUATLD (2003) *Anti-tuberculosis drug resistance in the world: third global report* (WHO, Geneva)). Strains of bacterial bioweapons agents resistant to rifampicin can be, and have been, constructed (Lebedeva, et al. (1991) *Antibiot. Khimioter.* 36, 19-22; Pomerantsev, et al. (1993) *Antibiot. Khimioter.* 38, 34-38; Volger, et al. (2002) *Antimicrob. Agents Chemother.* 46, 511-513; Marianelli, et al. (204) *J. Clin. Microbiol.* 42, 5439-5443).

In view of the public-health threat posed by rifamycin-resistant bacterial infections, there is an urgent need for new antibacterial agents that target bacterial RNAP and an especially urgent need for new antibacterial agents that target bacterial RNAP derivatives resistant to known rifamycins. (See Chopra, et al. (2002) *J. Appl. Microbiol.* 92, 4S-15S; Darst, S (2004) *Trends Biochem. Sci.* 29, 159-162.)

SUMMARY OF THE INVENTION

The invention provides a new class of inhibitors of bacterial RNAP. Importantly, the invention provides inhibitors that can exhibit potencies higher than those of known inhibitors. Especially importantly, the invention provides inhibitors that can inhibit bacterial RNAP derivatives resistant to known inhibitors.

The invention provides bipartite inhibitors of bacterial RNAP that contain: (1) a first moiety that binds to the rifamycin binding site ("Rif pocket") of bacterial RNAP; (2) a second moiety that binds to the secondary channel of bacterial RNAP; and (3) a linker connecting said first and second moieties.

The bipartite inhibitors can interact with bacterial RNAP both through the first moiety and through the second moiety. Their ability to interact with bacterial RNAP through two moieties (both the first moiety and the second moiety) can confer an affinity for interaction with bacterial RNAP that is higher than the affinity of the first moiety and the affinity of the second moiety. Their ability to interact to interact with bacterial RNAP through two moieties (both the first moiety and the second moiety) also can confer an ability to interact with a bacterial RNAP derivative resistant to at least one of the first moiety and the second moiety.

The bipartite inhibitors have applications in control of bacterial gene expression, control of bacterial growth, antibacterial chemistry, and antibacterial therapy.

The invention also provides a method for preparing a compound that contains: (1) a first moiety that binds to the rifamycin binding site ("Rif pocket") of bacterial RNAP; (2) a second moiety that binds to the secondary channel of bacterial RNAP; and (3) a linker connecting said first and second moieties. The method includes providing precursors X-α' and 'α-Y, and reacting moieties α' and 'α to form α.

For example, one precursor may contain an activated ester and the other precursor contain an amine. One precursor may contain a haloacetyl moiety and the other precursor contain an amine. One precursor may contain a haloacetyl moiety and the other precursor contain a sulfhydryl. One precursor may contain an azide and the other precursor contain an alkyne. One precursor may contain an azide and the other precursor contain a phosphine. One precursor may contain a boronic acid and the other precursor contain a substituted phenol. One precursor may contain a phenylboronic acid and the other precursor contain salicylhydroxamic acid.

These and other aspects of the present invention will be better appreciated by reference to the following drawings and Detailed Description.

BRIEF DESCRIPTION OF THE DRAWINGS

Figure 1:
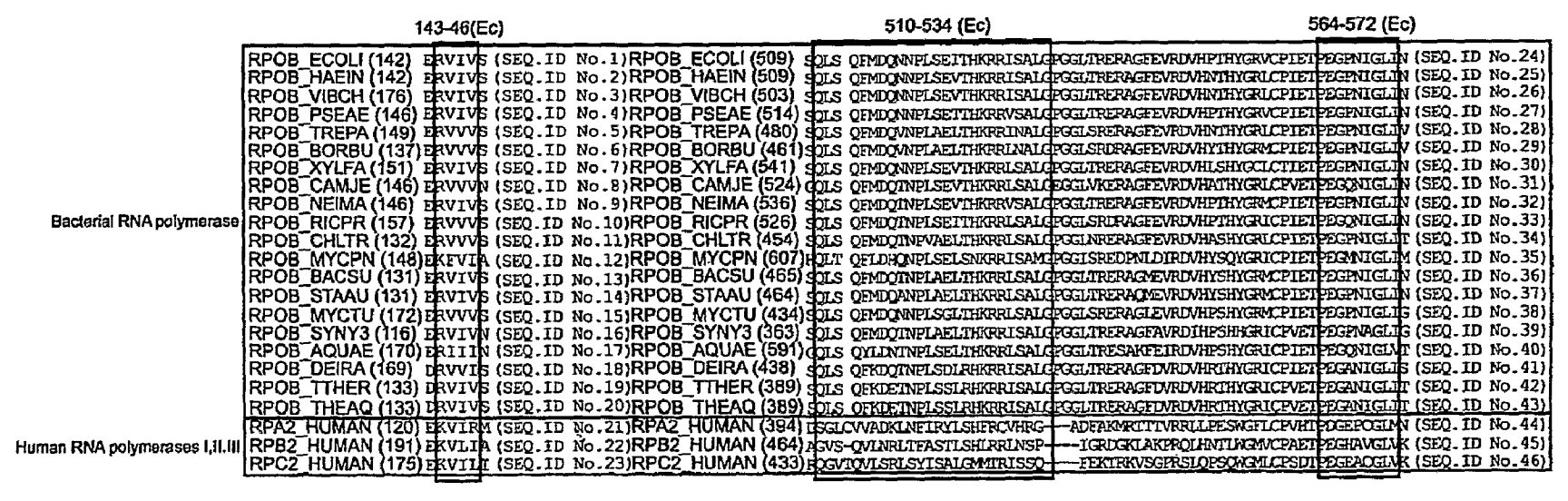

FIG. 1 shows a sequence alignment defining the Rif pocket of bacterial RNAP. The sequence alignment shows amino acid residues 136-146, 510-534, and 564-572 of the β subunit of RNAP from *Escherichia coli*; and corresponding residues of the β subunits of *Haemophilus influenzae, Vibrio cholerae, Pseudomonas aeruginose, Treponema pallidum, Borrelia burgdorferi, Xylella fastidiosa, Campylobacter jejuni, Neisseria meningitidis, Rickettsia prowazekii, Thermotoga maritime, Chlamydia trachomatis, Mycoplasma pneumoniae, Bacillus subtilis, Staphylococcus aureus, Mycobacterium tuberculosis, Synechocystis* sp., *Aquifex aeolicus, Deinococ-* cus radiodurans, Thermus thermophilus, and Thermus aquaticus (collectively, the "Rif pocket"); and corresponding residues of the second-largest subunits of human RNAP I, RNAP II and RNAP III.

Figure 2A:
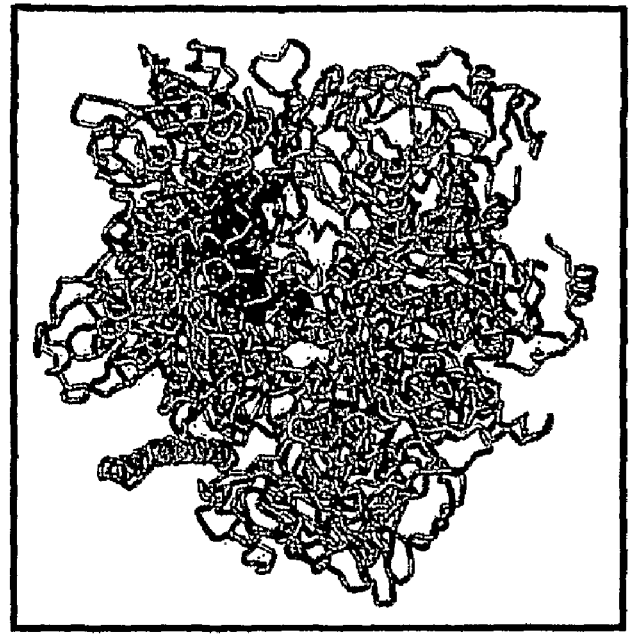
Figure 2B:
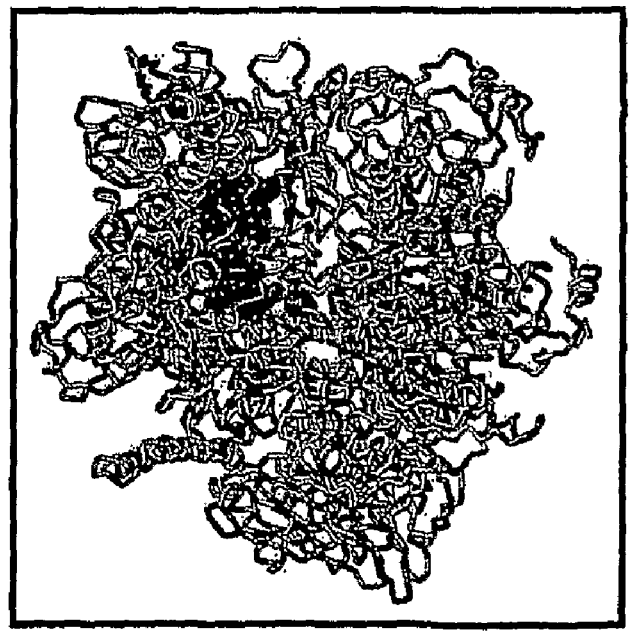

FIGS. 2A and 2B form a stereodiagram that show the position of the Rif pocket within the three-dimensional structure of bacterial RNAP.

Figure 3:
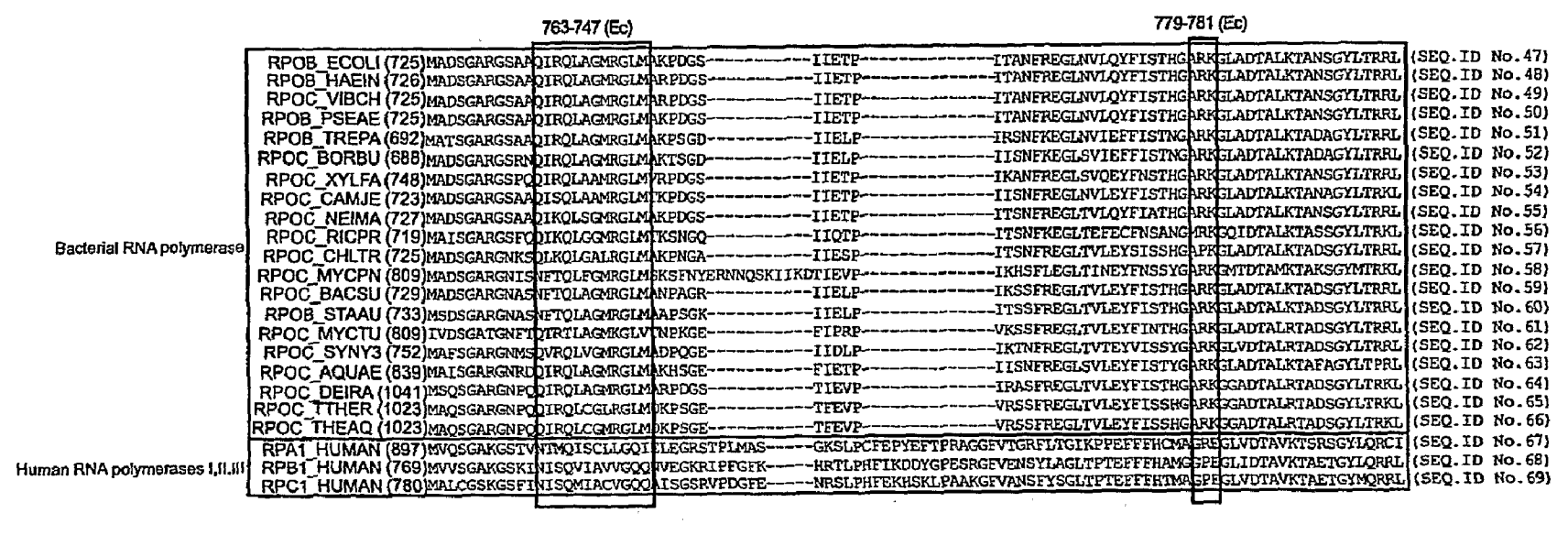

FIG. 3 shows a sequence alignment defining the homologous secondary channel amino acid sequence of bacterial RNAP. The sequence alignment shows amino acid residues 736-747 and 779-781 of the β' subunit of RNAP from *Escherichia coli*; and corresponding residues of the B' subunits of *Haemophilus influenzae, Vibrio cholerae, Pseudomonas aeruginose, Treponema pallidum, Borrelia burgdorferi, Xylella fastidiosa, Campylobacter jejuni, Neisseria meningitidis, Rickettsia prowazekii, Thermotoga maritime, Chlamydia trachomatis, Mycoplasma pneumoniae, Bacillus subtilis, Staphylococcus aureus, Mycobacterium tuberculosis, Synechocystis* sp., *Aquifex aeolicus, Deinococcus radiodurans, Thermus thermophilus*, and *Thermus aquaticus* (collectively, "the homologous secondary channel amino acid sequence"); and corresponding residues of the largest subunits of human RNAP I, RNAP II and RNAP III.

Figure 4A:
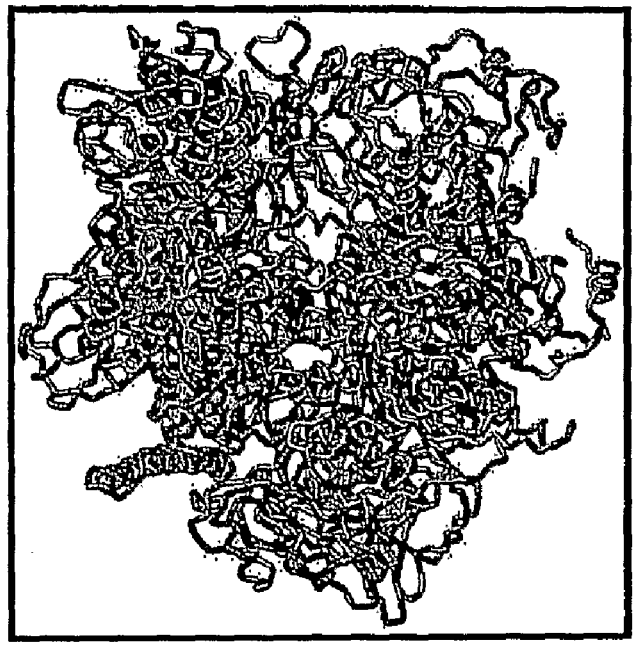
Figure 4B:
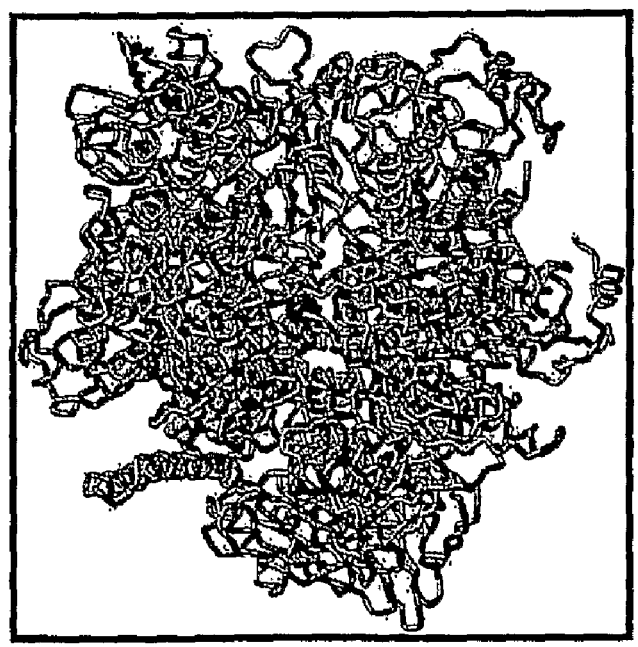

FIGS. 4A and 4B form a stereodiagram that show the position of the homologous secondary channel amino acid sequence within the three-dimensional structure of bacterial RNAP.

Figure 5A:
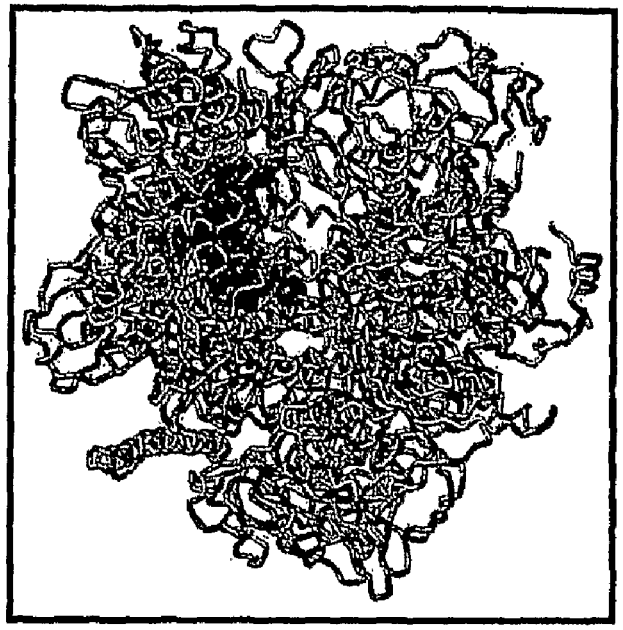
Figure 5B:
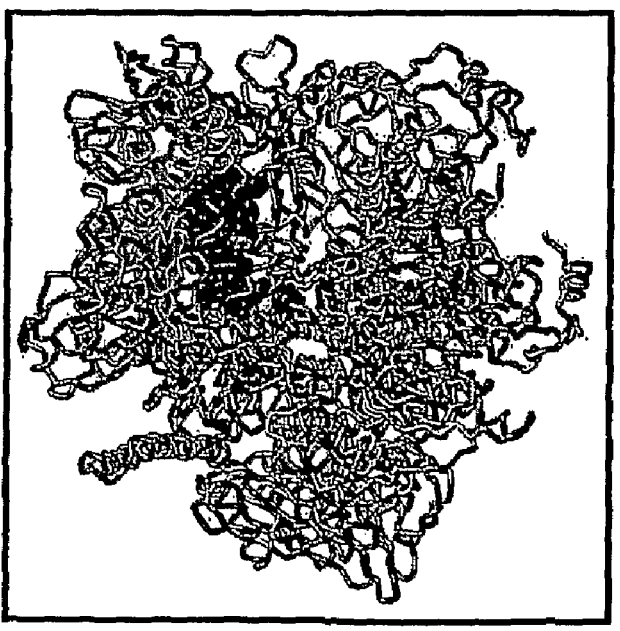

FIGS. 5A and 5B form a stereodiagram that show the relationship between the Rif pocket and the homologous secondary channel amino acid sequence within the three-dimensional structure of bacterial RNAP.

Figure 6A:
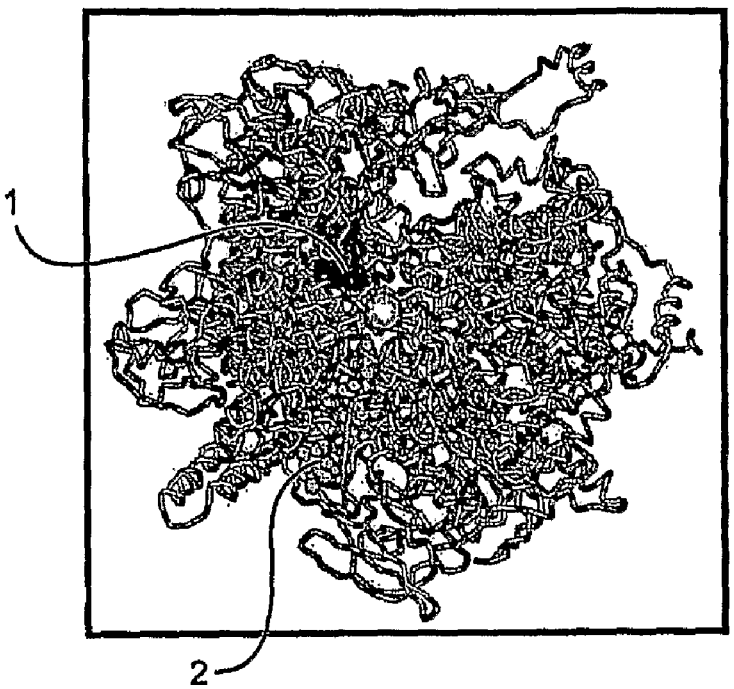
Figure 6B:
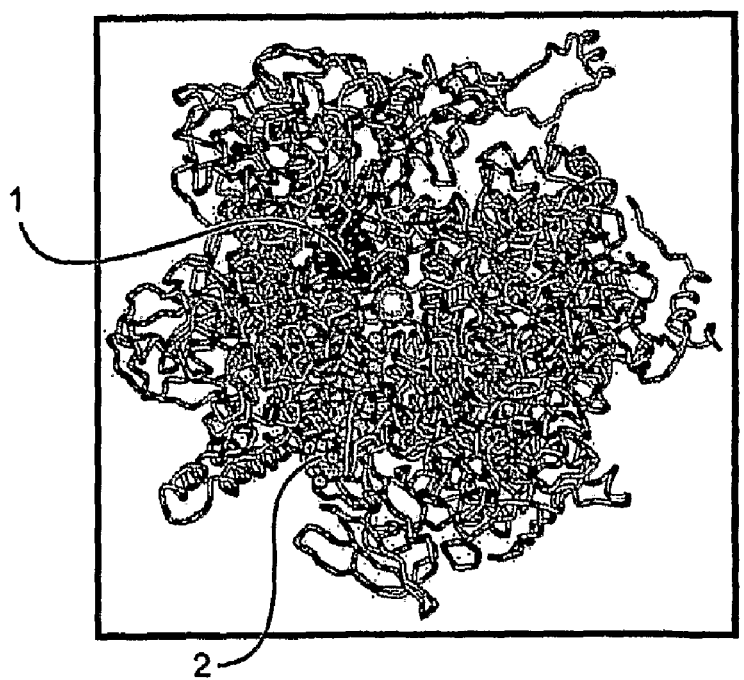

FIGS. 6A and 6B form a stereodiagram that show modeled structures of a bacterial RNAP in complex with rifamycin and MccJ25. Rifamycin is shown as the dark clustered spheres (1). MccJ25 is shown as the gray clustered spheres (2).

Figure 6C:
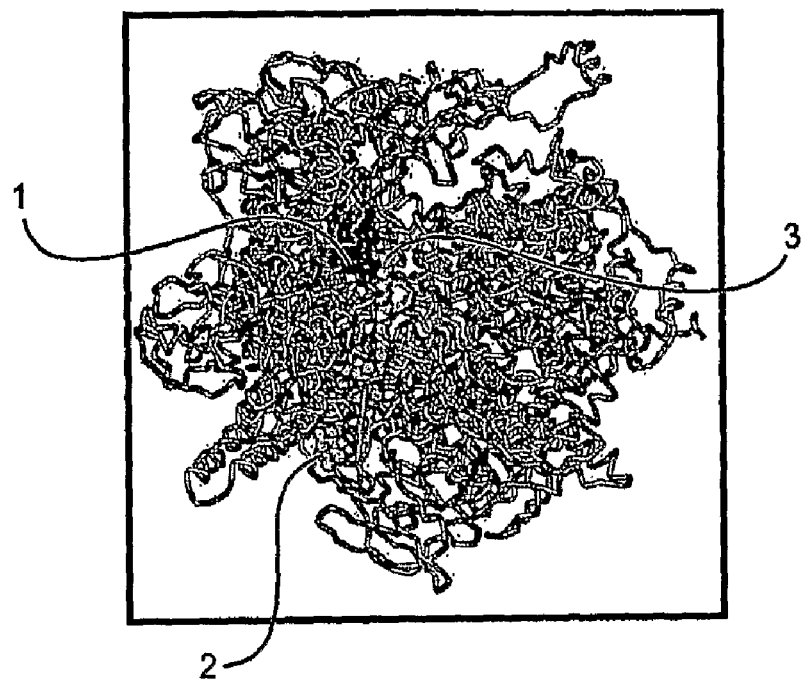
Figure 6D:
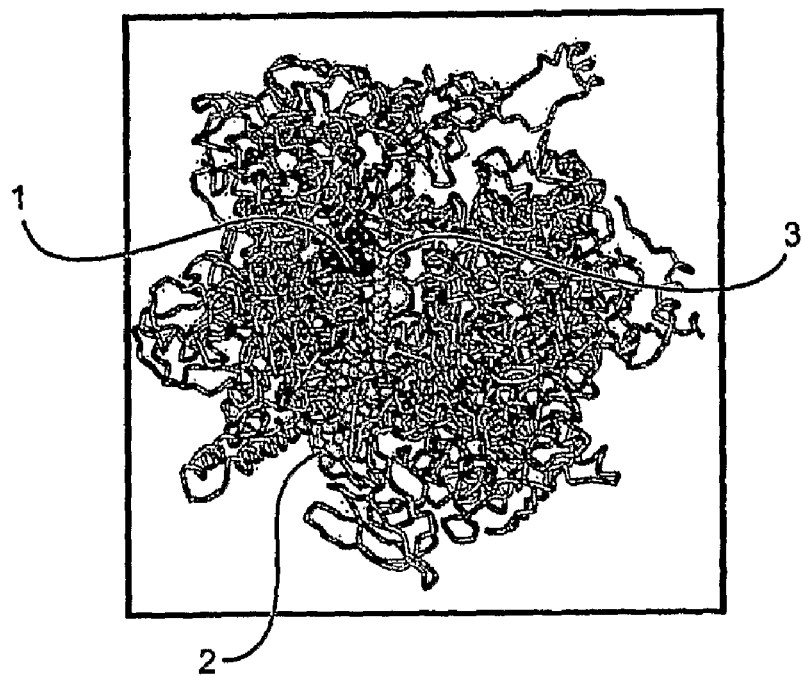

FIGS. 6C and 6D form a stereodiagram that show modeled structures of a bacterial RNAP in complex with a rifamicrocin The rifamycin moiety is shown as the dark clustered spheres (1). The MccJ25 moiety is shown as the gray clustered spheres (2). The connecting linker is shown as the very light clustered spheres (3).

Figure 7:
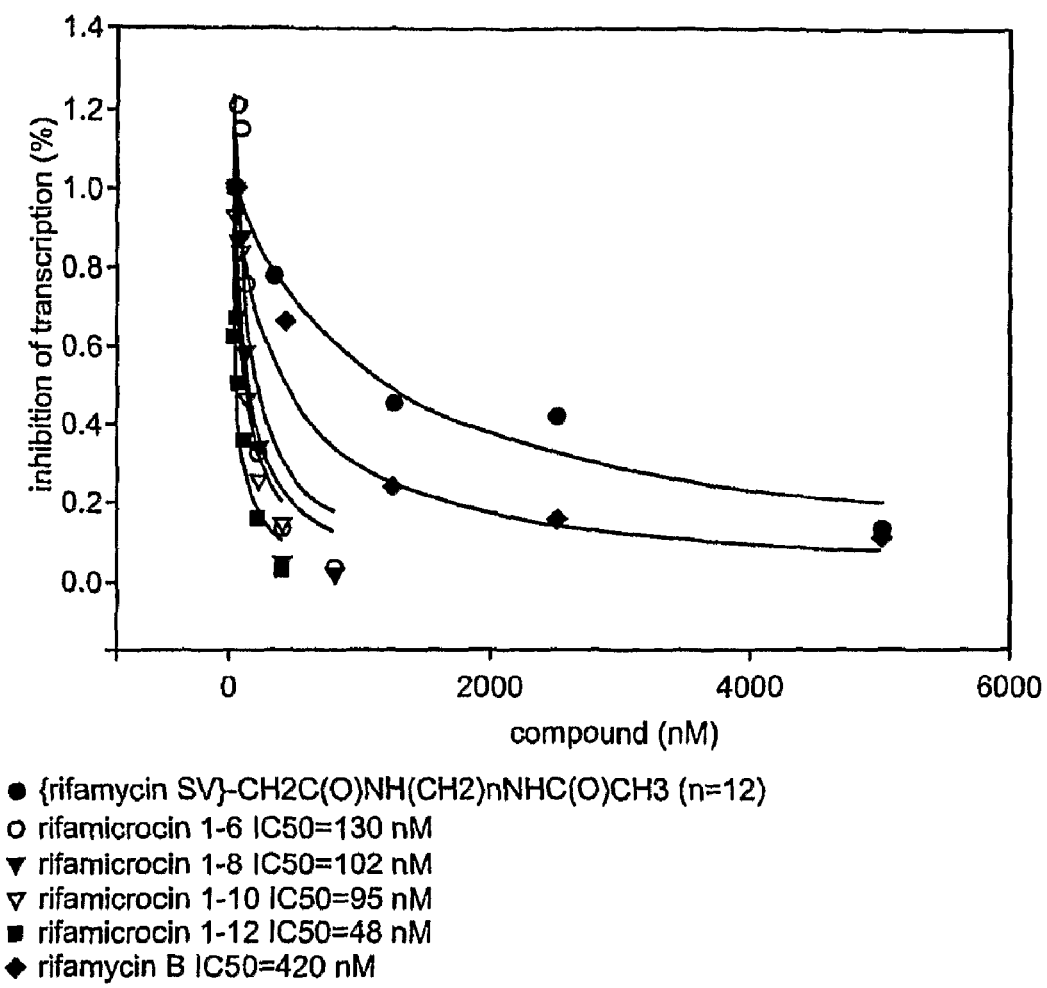

FIG. 7 shows effects of compounds on transcription by a rifamycin-resistant RNAP derivative, [Asn516]β-RNAP. Data are presented for compounds of this invention (rifamicrocin 1-6, rifamicrocin 1-8, rifamicrocin 1-10, and rifamicrocin 1-12; see Example 1.6); for the parent rifamycin ({rifamycin SV}—CH$_2$C(O)NH(CH$_2$)$_n$NHC(O)CH$_3$; see Example 1.3); and for a prior-art rifamycin (rifamycin B).

Figure 8:
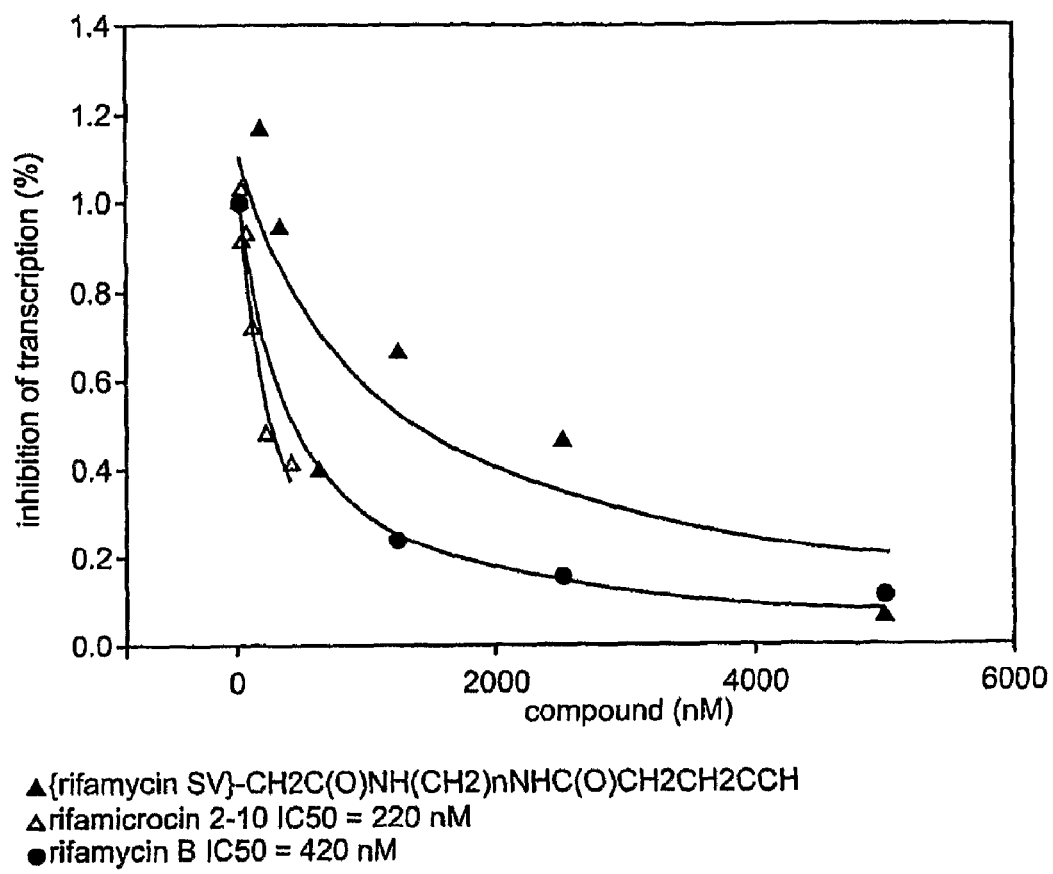

FIG. 8 shows effects of compounds on transcription by a rifamycin-resistant RNAP derivative, [Asn516]β-RNAP. Data are presented for a compound of this invention (rifamicrocin 2-10; see Example 2.6); for the parent rifamycin ({rifamycin SV}CH$_2$C(O)NH(CH$_2$)$_n$NHC(O)CH$_2$CH$_2$CCH; see Example 2.5); and for a prior-art rifamycin (rifamycin B).

BEST MODE OF CARRYING OUT THEE INVENTION

The present invention provides a compound that is a specific inhibitor of bacterial RNAP, the enzyme responsible for transcription. The compound has a structural formula

X is a moiety that binds to the Rif pocket of a bacterial RNA polymerase. Y is a moiety that binds to the secondary channel of a bacterial RNA polymerase. α is a linker. The invention has applications in control of bacterial gene expression, control of bacterial growth, antibacterial chemistry, and antibacterial therapy.

X Moiety that Binds to the Rif Pocket of RNAP:

A region located within the RNAP active-center cleft—a region that comprises amino acids 136-146, 510-534, and 564-572 of the RNAP β subunit in RNAP from *Escherichia coli*—is a useful target for compounds that inhibit transcription, including, by way of example, rifamycins, streptovaricins, tolypomycins, and sorangicins (Rinehart (1972) *Accts. Chem. Res.* 5, 57-64; Wehrli (1977) *Topics Curr. Chem.* 72, 21-49; Campbell, et al. (2001) *Cell* 104, 901-912; Artsimovitch, et al. (2005) *Cell* 122, 351-363; Floss, et al. (2005) *Chem. Rev.* 105, 621-632; STV: Rinehart (1972) *Accts. Chem. Res.* 5, 57-64; Wehrli (1977) *Topics Curr. Chem.* 72, 21-49; Nitta, et al. (1968) *J. Antibiotics* 21, 521-522; Morrow, et al. (1979) *J. Bacteriol* 137, 374-383; TOL: Kondo, et al. (1972) *J. Antibiotics* 25, 16-24; SOR: Rommelle, et al. (1990) *J. Antibiotics* 43, 88-91; O'Niell, et al. (2000) *Antimicrobial Agents Chemother.* 44, 3163-3166; Campbell, et al. (2005) *EMBO J.* 24, 1-9; FIG. 1). This region is referred to herein as the "Rif pocket," reflecting the fact that it serves as the binding site for rifamycins, among other compounds. The Rif pocket includes residues that are invariant or nearly invariant in RNAP from bacterial species, but that are radically different in RNAP from eukaryotic species (FIG. 1). The Rif pocket forms a ~10 Å shallow pocket within the wall of the RNAP active-center cleft (FIG. 2). A compound that binds to the Rif pocket of a bacterial RNAP can physically and/or allosterically block bacterial RNA synthesis, can inhibit bacterial gene expression, and can inhibit bacterial growth.

The Rif pocket referred to above in RNAP from *Escherichia coli* is similar in amino acid sequence in RNAP from most or all species of bacteria (FIG. 1). For example, amino acid residues 136-146, 510-534, and 564-572 of the β subunit of RNAP from *Escherichia coli* exhibit high similarity to amino acid residues 132-135, 466-490, and 520-528 of the β subunit of RNAP from *Bacillus subtilis* (FIG. 1). Thus, the discovery of a molecule that binds to the Rif pocket of, and inhibits RNA synthesis by, RNAP from *Escherichia coli* also is likely to bind to the Rif pocket of, and inhibit RNA synthesis by, RNAP from other species of bacteria. Therefore, molecules found to have antibacterial activity (through binding to the Rif pocket and inhibiting RNA synthesis) against *Escherichia coli* are likely to be found to have antibacterial activity against other species of bacteria.

In contrast, the Rif pocket differs radically in amino acid sequence between bacterial RNAP and eukaryotic RNAP, including human RNAP I, human RNAP II, and human RNAP III (FIG. 1). This allows for the identification of molecules that bind, in a Rif-pocket-dependent fashion, to a bacterial RNAP, but that do not bind, or that bind substantially less well, to a eukaryotic RNAP. This also allows for the identification of molecules that inhibit, in a Rif-pocket-dependent fashion, an activity of a bacterial RNAP, but that do not inhibit, or that inhibit substantially less well, an activity of a eukaryotic RNAP. This differentiation is important, because it permits the identification of bacterial-RNAP-selective binding molecules and bacteria-selective inhibitors.

Ligands that bind to the Rif pocket of, and inhibit RNA synthesis by, a bacterial RNAP are known in the art. Such ligands include, for example, rifamycins (a class of compounds that includes, for example, rifampicin, rifapentine, rifabutin, rifamycin B, and rifamycin SV), streptovaricins, tolypomycins, and sorangicins (Rinehart (1972) *Accts. Chem. Res.* 5, 57-64; Wehrli (1977) *Topics Curr. Chem.* 72, 21-49; Campbell, et al. (2001) *Cell* 104, 901-912; Artsimovitch, et al. (2005) *Cell* 122, 351-363; Floss, et al. (2005) *Chem. Rev.* 105, 621-632; STV: Rinehart (1972) *Accts. Chem. Res.* 5, 57-64; Wehrli (1977) *Topics Curr. Chem.* 72, 21-49; Nitta, et al. (1968) *J. Antibiotics* 21, 521-522; Morrow, et al. (1979) *J. Bacteriol.* 137, 374-383; TOL: Kondo, et al. (1972) *J. Antibiotics* 25, 16-24; SOR: Rommelle, et al. (1990) *J. Antibiotics* 43, 88-91; O'Niell, et al. (2000) *Antimicrobial Agents Chemother.* 44, 3163-3166; Campbell, et al. (2005) *EMBO J.* 24, 1-9) The references cited above are incorporated herein in their entirety.

The X moiety is a moiety that binds to the Rif pocket of a bacterial RNAP.

The X moiety can be any ligand that binds to the Rif pocket of a bacterial RNAP.

In a preferred embodiment, the X moiety is selected from the group consisting of a rifamycin derivative, a streptovaricin derivative, a tolypomycin derivative, or a sorangicin derivative.

In a preferred embodiment, X is a rifamycin derivative.

When X is a rifamycin derivative, it is preferred that X is bonded to the α linker through the rifamycin napthol group, most preferably, through at least one of the O12 atom, the C3 atom, and the C4 atom [representing atoms that, in the three-dimensional structure of RNAP-rifamycin complexes (see Campbell, et al. (2001) *Cell* 104, 901-912; Artsimovitch, et al. (2005) *Cell* 122, 351-363), are not involved in RNAP-rifamycin interactions and thus that can be functionalized without loss of RNAP-rifamycin interactions].

By way of example, when X is a rifamycin derivative, X can be bonded to the α linker through one of an ester linkage or an ether linkage involving the rifamycin O12 atom. By way of further example, when X is a rifamycin derivative, X can be bonded to the α linker though an iminomethylenyl linkage involving the rifamycin C3 atom. By way of further example, when X is a rifamycin derivative, X can be bonded to the cc linker through a cyclo linkage involving the C3 and C4 atoms. Methods of functionalization of the rifamycin O12, C3, and C4 atoms are established and known in the art.

In another preferred embodiment, X is a streptovaricin derivative.

When X is a streptovaricin derivative, it is preferred that X is bonded to the cc linker through the streptovaricin napthol group, most preferably, through at least one of the O3 atom, the C3 atom, and the C4 atom [representing atoms that, by analogy to the three-dimensional structures of RNAP-rifamycin complexes (see Campbell, et al. (2001) *Cell* 104, 901-912; Artsimovitch, et al. (2005) *Cell* 122, 351-363), are expected not to be involved in RNAP-streptovaricin interactions and thus to be able to be functionalized without loss of RNAP-streptovaricin interactions].

In another preferred embodiment, X is a tolypomycin derivative.

When X is a tolypomycin derivative, it is preferred that X is bonded to the cc linker through the tolypomycin napthoquinone group, most preferably, through at least one of the O3 or N3 atom, the C3 atom, and the C4 atom [representing atoms that, by analogy to the three-dimensional structures of RNAP-rifamycin complexes (see Campbell, et al. (2001) *Cell* 104, 901-912; Artsimovitch, et al. (2005) *Cell* 122, 351-363) are expected not to be involved in RNAP-tolypomycin interactions and thus to be able to be functionalized without loss of RNAP-tolypomycin interactions].

In another preferred embodiment, X is a sorangicin derivative.

When X is a sorangicin derivative, it is preferred that X is bonded to the α linker through the sorangicin pendant side-chain group [corresponding to atoms C37-C45 and O10-O11 in sorangicin A, and representing a group that, in the three-dimensional structure of the RNAP-sorangicin-A complex (see Campbell, et al. (2005) *EMBO J.* 24, 1-9), are not involved in RNAP-sorangicin interactions and thus can be functionalized without loss of RNAP-sorangicin interactions].

Y Moiety that Binds to the Secondary Channel of RNAP:

Recently, crystallographic structures have been determined for bacterial RNAP and eukaryotic RNAP II (Zhang et al., (1999) *Cell* 98, 811-824; Cramer et al., (2000) *Science* 288, 640-649; Cramer et al., (2001) *Science* 292, 1863-1876; Gnatt et al., (2001 *Science* 292, 1876-1882; and Ebright, R. (2000) *J. Mol. Biol.* 304, 687-689), and, based on the crystallographic structures, biophysical results, and biochemical results, models have been proposed for the structures of transcription initiation and elongation complexes (Gnatt et al., (2001 *Science* 292, 1876-1882; Ebright, R. (2000) *J. Mol. Biol.* 304, 687-689; Naryshkin et al., (2000 *Cell* 101, 601-611; Kim et al., (2000) *Science* 288, 1418-1421; Korzheva et al., (2000) *Science* 289, 619-625; and Mekler et al., (2002) *Cell* 108:599-614).

The models for the transcription elongation complex imply that nucleic acids completely fill the active-center cleft of RNAP, and thus the only route by which incoming nucleoside-triphosphate substrates ("NTPs") can access the active center is through a ~25 Å long, ~10 Å wide tunnel—the "secondary channel" or "pore"—that bores through the floor of the active-center cleft of RNAP and extends to the exterior surface of RNAP opposite the active-center cleft (Gnatt et al., (2001) *Science* 292, 1876-1882; Ebright, R. (2000) *J. Mol. Biol.* 304, 687-689; and Korzheva et al., (2000) *Science* 289, 619-625).

The models for the transcription elongation complex imply that the RNAP secondary channel mediates multiple biochemical activities important for function of RNAP, including: uptake of NTPs, release of pyrophosphate product, release of abortive-RNA and edited-RNA products, interaction with RNA product during transcriptional pausing, interaction with RNA product during transcriptional arrest, interaction with RNA product during editing, and interaction with the elongation factors GreA and GreB.

Physically blocking the RNAP secondary channel with a small molecule can inhibit one or more of these activities and thereby can inhibit function of RNAP (WO 2004/023093; Mukhopadhyay et al. (2004) *Mol. Cell* 14, 739-751; Adelman et al. (2004) *Mol. Cell* 14, 753-762). For example, physically blocking the RNAP secondary channel with a small molecule can prevent uptake of NTPs by RNAP and thus can prevent transcription (WO 2004/023093; Mukhopadhyay et al. (2004) *Mol. Cell* 14, 739-751; Adelman et al. (2004) *Mol. Cell* 14, 753-762).

A region within the RNAP secondary channel—a region that comprises amino acids 736-747 and 779-781 of the RNAP β' subunit in RNAP from *Escherichia coli*—is a useful target for compounds that inhibit transcription, including, by way of example, the lariat peptide microcin J25 (MccJ25) and derivatives thereof (WO 2004/023093; FIG. 3). This region includes residues that are invariant or nearly invariant in RNAP from bacterial species, but that are radically different in RNAP from eukaryotic species (FIG. 3). This region forms a ~5 Å shallow pocket within the wall of the RNAP secondary channel (FIG. 4). A compound that binds to this region of a bacterial RNAP can physically block the secondary channel of a bacterial RNAP, can prevent uptake of NTPs by a bacterial RNAP, can inhibit bacterial transcription, can inhibit bacterial gene expression, and can inhibit bacterial growth.

The secondary-channel region referred to above in RNAP from *Escherichia coli* is similar in amino acid sequence in RNAP from most or all other species of bacteria and is called herein the "homologous secondary channel amino acid sequence" (FIG. 3). (For example, amino acid residues 736-747 and 779-781 of the β' subunit of RNAP from *Escherichia coli* exhibit high similarity to amino acid residues 740-751 and 783-785 of the β' subunit of RNAP from *Bacillus subtilis* (FIG. 3). Thus, the discovery of a molecule that binds to this region and inhibits an activity associated with the secondary channel in RNAP from *Escherichia coli* also is likely to bind to this region and inhibit an activity associated with the secondary channel in RNAP from other species of bacteria. Therefore, molecules found to have antibacterial activity (through binding to this region and inhibiting an activity associated with the secondary channel) against *Escherichia coli* are likely to be found to have antibacterial activity against other species of bacteria.

In contrast, the secondary-channel region referred to above differs radically in amino acid sequence between bacterial RNAP and eukaryotic RNAP, including human RNAP I, human RNAP II, and human RNAP III (FIG. 3). This allows for the identification of molecules that bind, in a secondary-channel-region-dependent fashion, to a bacterial RNAP, but that do not bind, or that bind substantially less well, to a eukaryotic RNAP. This also allows for the identification of molecules that inhibit, in a secondary-channel region-dependent fashion, an activity of a bacterial RNAP, but that do not inhibit, or that inhibit substantially less well, an activity of a eukaryotic RNAP. This differentiation is important, because it permits the identification of bacterial-RNAP-selective binding molecules and bacteria-selective inhibitors.

In the three-dimensional structure of a bacterial RNAP, the secondary-channel region referred to above is located near to, but does not overlap, the Rif pocket (FIG. 5). The distance between the center of the secondary-channel region referred to above and the center of the Rif pocket is ~25 Å.

The invention provides, by way of example only, a bacterial RNAP homologous secondary channel amino acid sequence corresponding to, and alignable with, residues 736-747 and 779-781 of the β' subunit of RNAP from *Escherichia coli*, as well as with corresponding residues of the 13 subunit of *Bacillus subtilis, Haemophilus influenzae, Vibrio cholerae, Pseudomonas aeruginosa, Treponema pallidum, Borrelia burgdorferi, Xylella fastidiosa, Campylobacter jejuni, Neisseria meningitidis, Rickettsia prowazekii, Thermotoga maritima, Chlamydia trachomatis, Mycoplasma pneumoniae, Staphylococcus aureus, Mycobacterium tuberculosis, Synechocystis* sp., *Aquifex aeolicus, Deinococcus radiodurans, Thermus thermophilus*, and *Thermus aquaticus*.

Ligands that bind to the secondary channel of, and inhibit an activity of, a bacterial RNAP are known in the art. Such ligands include, for example, the lariat peptide microcin J25 (MccJ25)(WO 2004/023093; Mukhopadhyay et al. (2004) *Mol. Cell* 14, 739-751; Adelman, et al. (2004) *Mol. Cell* 14, 753-762; Bayro, et al. (2003) *J. Am. Chem. Soc.* 125, 12382-12383; Rosengren, et al. (2003) *J. Am. Chem. Soc.* 125, 12464-12474; Wilson, et al. (2003) *J. Am. Chem. Soc.* 125, 12475-12483), substituted derivatives of the lariat-peptide MccJ25 (WO 2004/023093; U.S. application Ser. No. 11/371,736, filed Mar. 9, 2006; Mukhopadhyay, et al. (2004) *Mol. Cell* 14, 739-751), minimized derivatives of lariat peptide MccJ25 (WO2005/024040; Semenova, et al. (2005) *J. Bacteriol.* 187:3859-3863), the non-peptide inhibitor tagetitoxin (Vassylyev, et al. (2005) *Nature Structl. Mol. Biol.* 12, 1086-1093), and the non-peptide inhibitor ppGpp (Artsimovitch, et al. (2004) *Cell* 117, 299-310). The references cited above are incorporated herein in their entirety.

The Y moiety is a moiety that binds to the secondary channel of a bacterial RNAP.

In a preferred embodiment, the Y moiety comprises an entity that binds to RNAP in the secondary channel of a bacterial RNAP and prevents RNAP from carrying out at least one biochemical activity with which the secondary channel is associated (e.g., at least one of uptake of NTP substrates, release of pyrophosphate product, release of edited nucleotide and oligonucleotide products, interaction with RNA product during transcriptional pausing, interaction with RNA product during transcriptional arrest, interaction with RNA product during editing, and interaction with the elongation factors GreA and GreB).

In a preferred embodiment, the Y moiety comprises an entity that that binds to the homologous secondary channel amino acid sequence of a bacterial RNAP. Thus, in one preferred embodiment, the Y moiety comprises an entity that binds to at least one residue of a homologous secondary channel amino acid sequence corresponding to, and alignable with, residues 736-747 and 779-781 of the β' subunit of RNAP from *Escherichia coli*, as well as with corresponding residues of the β' subunit of *Bacillus subtilis, Haemophilus influenzae, Vibrio cholerae, Pseudomonas aeruginosa, Treponema pallidum, Borrelia burgdorferi, Xylella fastidiosa, Campylobacter jejuni, Neisseria meningitidis, Rickettsia prowazekii, Thermotoga maritima, Chlamydia trachomatis, Mycoplasma pneumoniae, Staphylococcus aureus, Mycobacterium tuberculosis, Synechocystis* sp., *Aquifex aeolicus, Deinococcus radiodurans, Thermus thermophilus*, and *Thermus aquaticus*.

Methods for identifying ligands that bind to the secondary channel of a bacterial RNAP, through use of assays for ligands that bind to a bacterial RNAP in a secondary-channel-dependent fashion, are disclosed in WO 2004/023093, published Mar. 18, 2004 incorporated herein by reference. For example, *Escherichia coli* RNAP, or a fragment thereof containing the secondary channel, can be used as the test protein for binding, and a derivative of the RNAP, or RNAP fragment, having at least one of a substitution, an insertion, or a deletion within the secondary channel can be used as the control protein for secondary-channel-dependence of binding. "Hits" can be analyzed for binding and inhibition of Gram-negative-bacterial RNAP, Gram-positive-bacterial RNAP, and eukaryotic RNAP I, RNAP III and RNAP III, in vivo and in vitro. "Hits" also can be characterized structurally by x-ray diffraction analysis of co-crystals with RNAP or a fragment thereof containing the secondary channel.

The Y moiety can be any ligand that binds to the secondary channel of a bacterial RNAP.

Ligands that bind to the secondary channel of a bacterial RNAP include, but are not limited to, the lariat peptide MccJ25, derivatives of the lariat-peptide MccJ25, the non-peptide inhibitor tagetitoxin, and the non-peptide inhibitor ppGpp. The lariat peptide MccJ25 is further described in WO 2004/023093; Mukhopadhyay et al. (2004) *Mol. Cell* 14, 739-751; Adelman, et al. (2004) *Mol. Cell* 14, 753-762; Bayro, et al. (2003) *J. Am. Chem. Soc.* 125, 12382-12383; Rosengren, et al. (2003) *J. Am. Chem. Soc.* 125, 12464-12474; Wilson, et al. (2003) *J. Am. Chem. Soc.* 125, 12475-12483, Derivatives of the lariat-peptide MccJ25 are further described in WO2005/024040; U.S. application Ser. No. 11/371,736, filed Mar. 9, 2006; Mukhopadhyay, et al. (2004) *Mol. Cell* 14, 739-751; Semenova, et al. (2005) *J. Bacteriol.* 187:3859-3863. The non-peptide inhibitor tagetitoxin is further described in Vassylyev, et al. (2005) *Nature Structl. Mol.*

Biol. 12, 1086-1093. The non-peptide inhibitor ppGpp is further described in Artsimovitch, et al. (2004) *Cell* 117, 299-310. The references cited above are incorporated herein in their entirety.

In a preferred embodiment, the Y moiety is a derivative of a lariat peptide that binds to a bacterial RNAP secondary channel. In a further preferred embodiment, the Y moiety is a derivative of a lariat peptide that binds to at least one residue of a bacterial RNAP homologous secondary channel amino acid sequence.

In a preferred embodiment, the Y moiety is a derivative of the lariat peptide McCJ25. Such derivatives include analogs of McCJ25 having an amino acid sequence that differs by having at least one substitution, insertion or deletion and that binds bacterial RNAP and inhibits bacterial RNAP activity (see WO 2004/023093 incorporated herein by reference). Such derivatives also include analogs of McCJ25 that: (1) contains a discontinuity in the peptide backbone between residues 8 and 19; and (2) lacks one to about ten residues from the set consisting of residues 9-18 (see WO 2005/024040 incorporated herein by reference). Such derivatives also include analogs of McCJ25 generated through mutational scanning (see U.S. application Ser. No. 11/371,736, filed Mar. 9, 2006, incorporated herein by reference).

In a preferred embodiment, when Y is a McCJ25 derivative, the Y moiety can be bonded to the α linker through, by way of example, McCJ25 residue 5. (Two aspects of McCJ25 residue 5 make it suitable as a point of attachment of the α moiety. First, in the modelled structure of the RNAP-McCJ25 complex, McCJ25 residue 5 is in the portion of McCJ25 located closest to the Rif pocket (see Mukhopadhyay et al. (2004) *Mol. Cell* 14, 739-751). Second, McCJ25 residue 5 can be substituted without loss of affinity for RNAP and without loss of antibacterial activity (see U.S. application Ser. No. 11/371, 736, filed Mar. 9, 2006)). For example, when the Y moiety is [Lys5]McCJ25, the Y moiety can be bonded to the α linker through the Lys5 NZ atom of [Lys5]McCJ25.

α Linker:

α is a linker that links the X moiety that binds to the Rif pocket of a bacterial RNAP and the Y moiety that binds to the secondary channel of a bacterial RNAP. The linker preferably has a length of from about 15 Å to about 35 Å (representing a length suitable to connect a moiety bound to the Rif pocket of a bacterial RNAP and a moiety bound within the secondary channel of a bacterial RNAP; FIGS. 6A-D).

The linker may contain exclusively covalent bonds. Alternatively, the linker may contain a coordinate-covalent bond.

Preferably, the linker does not substantially interfere with the interaction between the X moiety and the Rif pocket of a bacterial RNAP and does not substantially interfere with the interaction between the Y moiety and the secondary channel of a bacterial RNAP. Optionally, the linker makes a favorable interaction with at least one residue of RNAP located between the Rif pocket and the secondary channel.

Bipartite Inhibitors of RNAP:

The invention provides, solely by way of example, bipartite inhibitors comprising a rifamycin moiety, a microcin J25 (McCJ25) moiety, and a covalent linker. Such bipartite inhibitors are referred to herein as "rifamicrocins" (rifamycin-microcins; FIGS. 6C, 6D).

We have found that rifamicrocins having the general formula {rifamycin SV}—{$CH_2C(O)NH(CH_2)_nNHC(O)CH_2S(CH_2)_3C(NH_2^+)$}-{[Lys5]microcin J25}, where n is an integer from about 4 to about 18 (referred to herein as "rifamicrocin 1-n"), inhibit *Escherichia coli* RNAP with high potencies, and inhibit a rifamycin-resistant derivative of *Escherichia coli* RNAP—[Asn516]βRNAP—with potencies higher than those of the parent rifamycin ($IC_{50}$~48-130 μM vs. $IC_{50}$~1200 μM). By way of example, the rifamicrocin having the formula {rifamycin SV}—{$CH_2C(O)NH(CH_2)_{12}NHC(O)CH_2S(CH_2)_3C(NH_2^+)$}-{[Lys5]microcin J25}(referred to herein as "rifamicrocin 1-12"), inhibits *Escherichia coli* RNAP with a high potency ($IC_{50}$=2 nM), and inhibits a rifamycin-resistant derivative of *Escherichia coli* RNAP—[Asn516]β RNAP—with a potency 25 times higher than that of the parent rifamycin ($IC_{50}$=48 μM vs. $IC_{50}$=1200 μM).

We have found that rifamicrocins having the general formula {rifamycin SV}—{$CH_2C(O)NH(CH_2)_nNHC(O)(CH2)_2(C_2N_3)(CH_2)_4C(O)$}-{[Lys5]microcin J25}, where n is an integer from about 2 to about 16 (referred to herein as "rifamicrocin 2-n"), likewise inhibit a rifamycin-resistant derivative of *Escherichia coli* RNAP—[Asn516]13 RNAP— with potencies higher than those of the parent rifamycin. By way of example, the rifamicrocin having the formula {rifamycin SV}—{$CH_2C(O)NH(CH_2)_{10}NHC(O)(CH2)_2(C_2N_3)(CH_2)_4C(O)$}-{[Lys5]microcin J25} (referred to herein as "rifamicrocin 2-10"), inhibits a rifamycin-resistant derivative of *Escherichia coli* RNAP—[Asn516]β RNAP—with a potency 5 times higher than that of the parent rifamycin ($IC_{50}$=220 μM vs. $IC_{50}$=1100 μM).

Method of Preparing Bipartite Inhibitors of RNAP:

The invention also provides a method of preparing a compound having a structural formula (I):

X-α-Y           (I)

wherein X is an moiety that binds to the Rif pocket of a bacterial RNA polymerase, Y is a moiety that binds to the secondary channel of a bacterial RNA polymerase, and α is a linker.

The method includes providing precursors X-α' and 'α-Y, and reacting moieties α' and 'α to form α.

The precursors may include any suitable precursors that will bind to form a linker moiety and permit the X moiety to bind to the Rif pocket of the RNAP and permit the Y moiety to bind to the secondary channel of the RNAP.

For example, in a preferred embodiment, one precursor contains an activated ester and the other precursor contains an amine. In another preferred embodiment, one precursor contains a haloacetyl moiety and the other precursor contains an amine. In another preferred embodiment, one precursor contains a haloacetyl moiety and the other precursor contains a sulfhydryl. In another preferred embodiment, one precursor contains an azide and the other precursor contains an alkyne. In another preferred embodiment, one precursor contains an azide and the other precursor contains a phosphine. In another preferred embodiment, one precursor contains a boronic acid and the other precursor contains a substituted phenol. In another preferred embodiment, one precursor contains phenylboronic acid and the other precursor contains salicylhydroxamic acid.

Each of the above-referenced chemistries are established and are known to those skilled in the art (see Rostovetsev, et al. (2002) *Angew. Chem. Int. Ed.* 41, 2596-2599 Wang, et al. (2003) *J. Amer. Chem. Soc.* 125, 3192-3193; Breibauer, et al. (2003) *ChemBioChem.* 4, 1147-1149; Saxon, et al. (2000) *Science* 287, 2007-2010; Kiick, et al. (2002), *Proc. Natl. Acad. Sci. USA* 99, 19-24; Kohn, et al. (2004) *Angew. Chem. Int. Ed.* 43, 3106-3116; Stolowitz, et al. (2001) *Bioconj. Chem.* 12, 229-239; Wiley, et al. (2001), 12, 240-250).

In one embodiment, moieties α' and 'α of precursors X-α' and 'α-Y are reacted in the absence of a bacterial RNA polymerase.

In another embodiment, moieties α' and 'α of precursors X-α' and 'α-Y are reacted in the presence of a bacterial RNA polymerase. In this embodiment, the bacterial RNA polymerase can serve as a template for reaction of X-α' and 'α-Y.

By way of example, {rifamycin SV}—{CH$_2$C(O)NH(CH$_2$)$_n$NHC(O)CH$_2$S(CH2)$_3$C(NH$_2^+$)}-{[Lys5]microcin J25}, where n is an integer from about 4 to about 18 (referred to herein as "rifamicrocin 1-n" [rifamycin-microcin, linker type 1, linker variable n] can be prepared by reacting: (1) {rifamycin SV}—{CH$_2$C(O)NH(CH$_2$)$_n$N—HC(O)CH$_2$Z, where n is an integer from about 4 to about 18, and Z is a halogen; and (2) HS(CH$_2$)$_3$C(NH$_2^+$)-{[Lys5]microcin J25}.

Scheme I below illustrates the synthesis of {rifamycin SV}—{CH$_2$C(O)NH(CH$_2$)$_n$NHC(O)CH$_2$Z, where n is an integer from about 4 to about 18, and Z is Br, and the synthesis of a corresponding "control" or "comparison" compound, {rifamycin SV}—{CH$_2$C(O)NH(CH$_2$)$_n$NHC(O)CH$_3$.

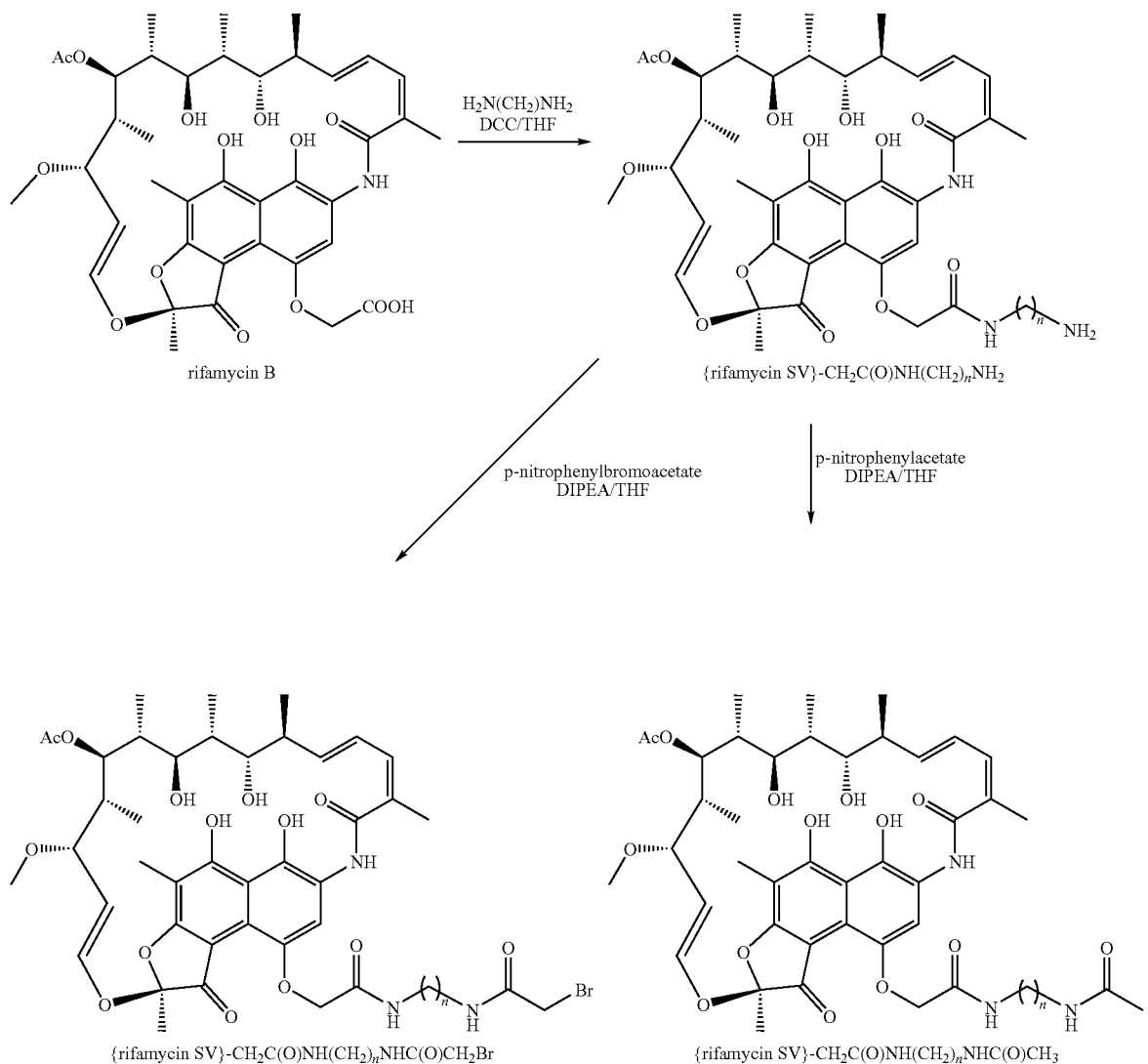

Scheme II below illustrates the synthesis of HS(CH$_2$)$_3$C(NH$_2^+$)-{[Lys5]MccJ25}.

Scheme II
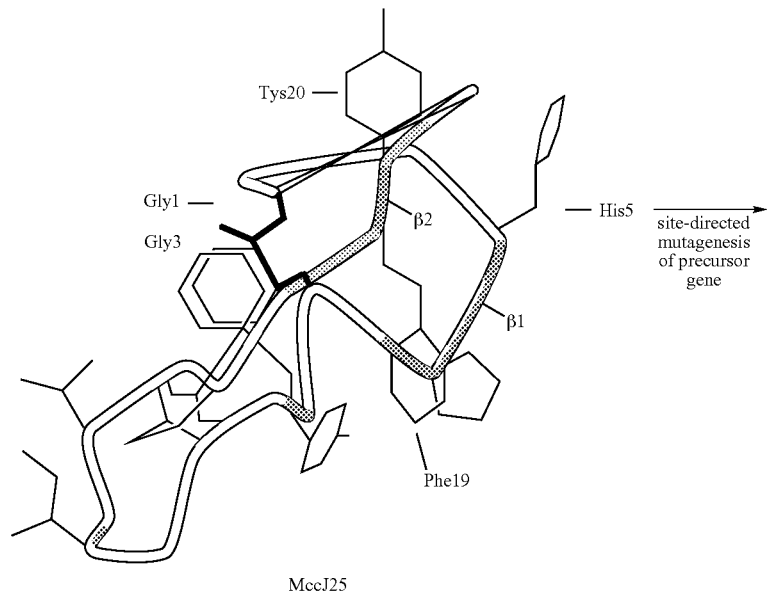
MccJ25
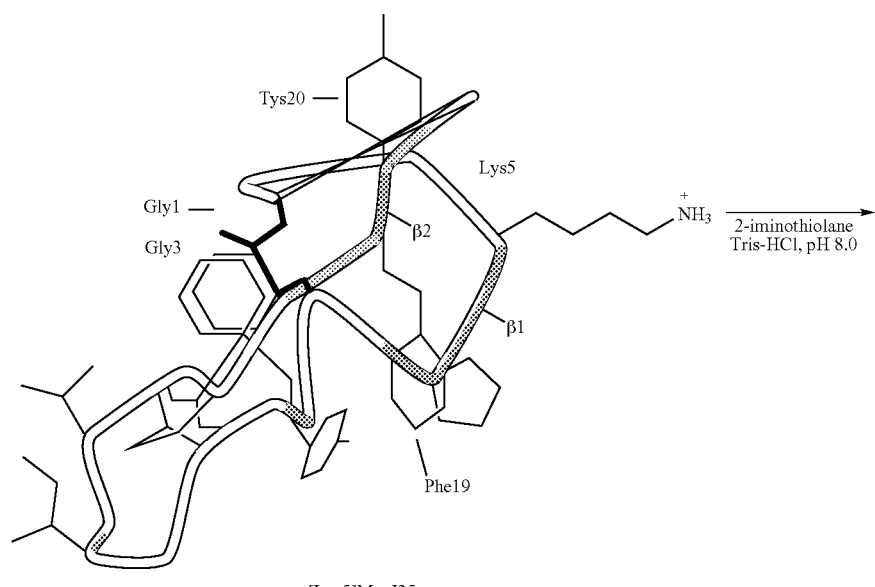
[Lys5]MccJ25

-continued

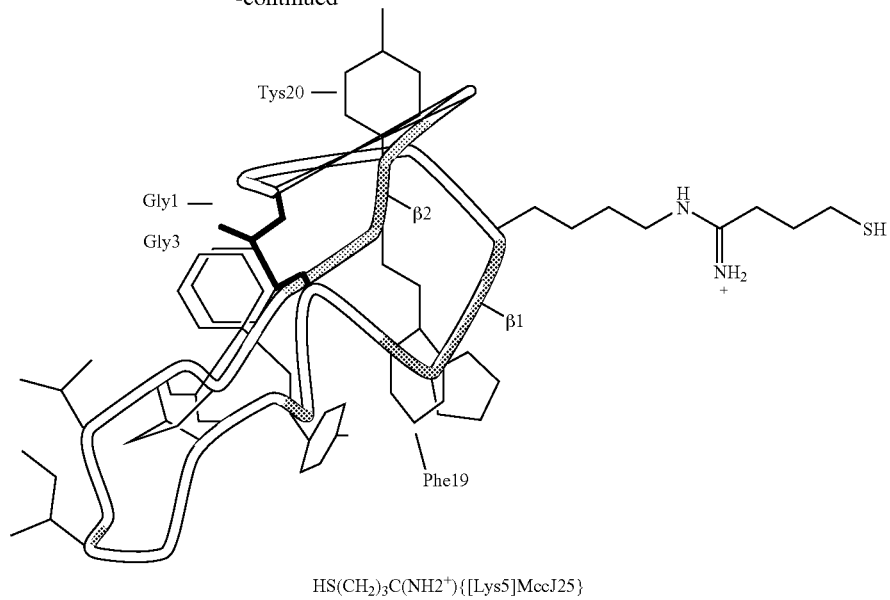

HS(CH$_2$)$_3$C(NH2$^+$){[Lys5]MccJ25}

Scheme III below illustrates the synthesis of {rifamycin SV}—{CH$_2$C(O)NH(CH$_2$)$_n$NHC(O)CH$_2$S(CH$_2$)$_3$C(NH$_2$$^+$)}-{[Lys5]microcin J25}, where n is an integer from about 4 to about 18 (referred to herein as "rifamicrocin 1-n" [rifamycin-microcin, linker type 1, linker variable n] by reacting: (1) {rifamycin SV}—{CH$_2$C(O)N—H(CH$_2$)$_n$NHC(O)CH$_2$Z, where n is an integer from about 4 to about 18, and Z is Br; and (2) HS(CH$_2$)$_3$C(NH$_2$$^+$)}-{[Lys5]microcin J25}.

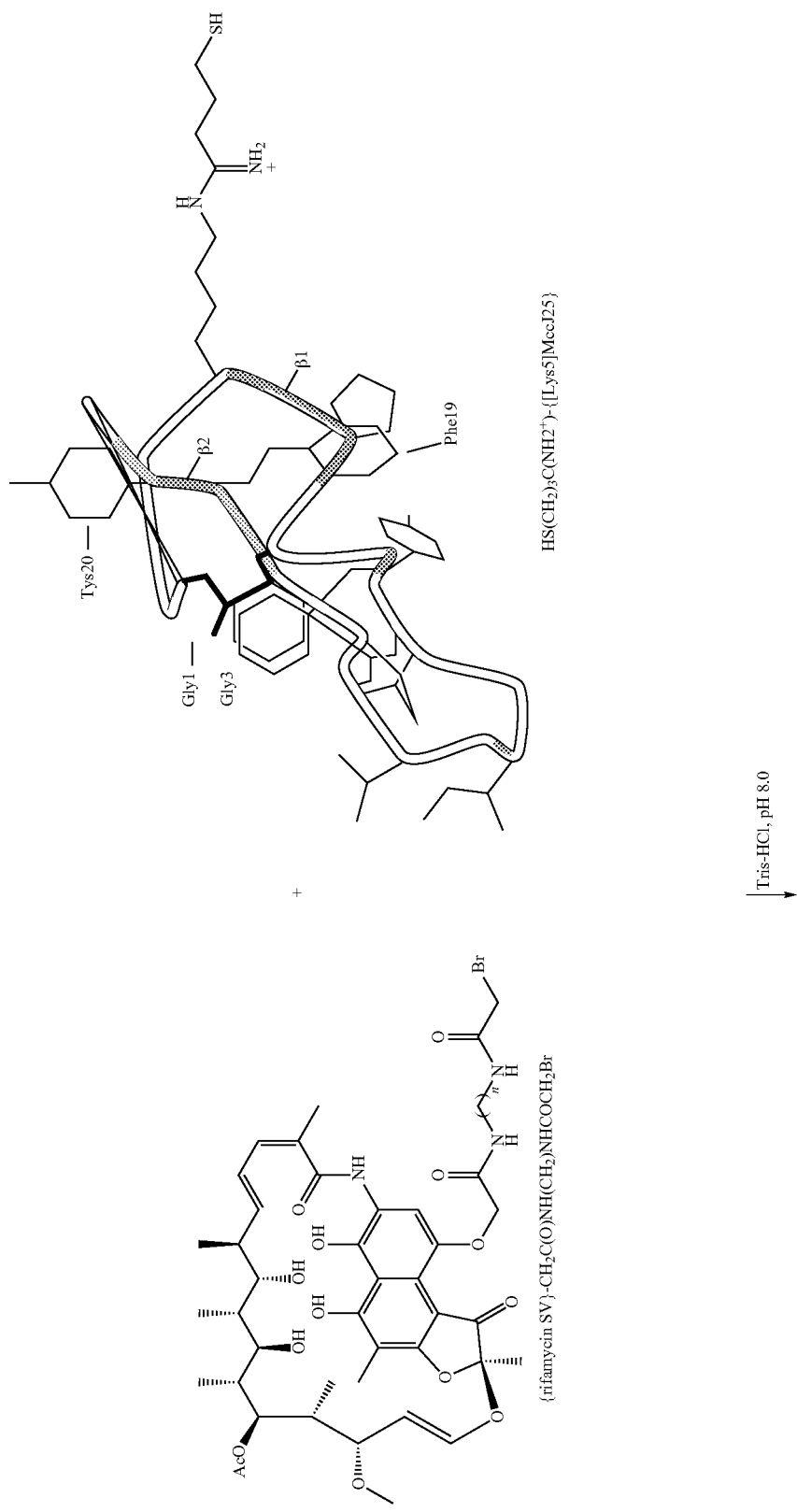
Scheme III

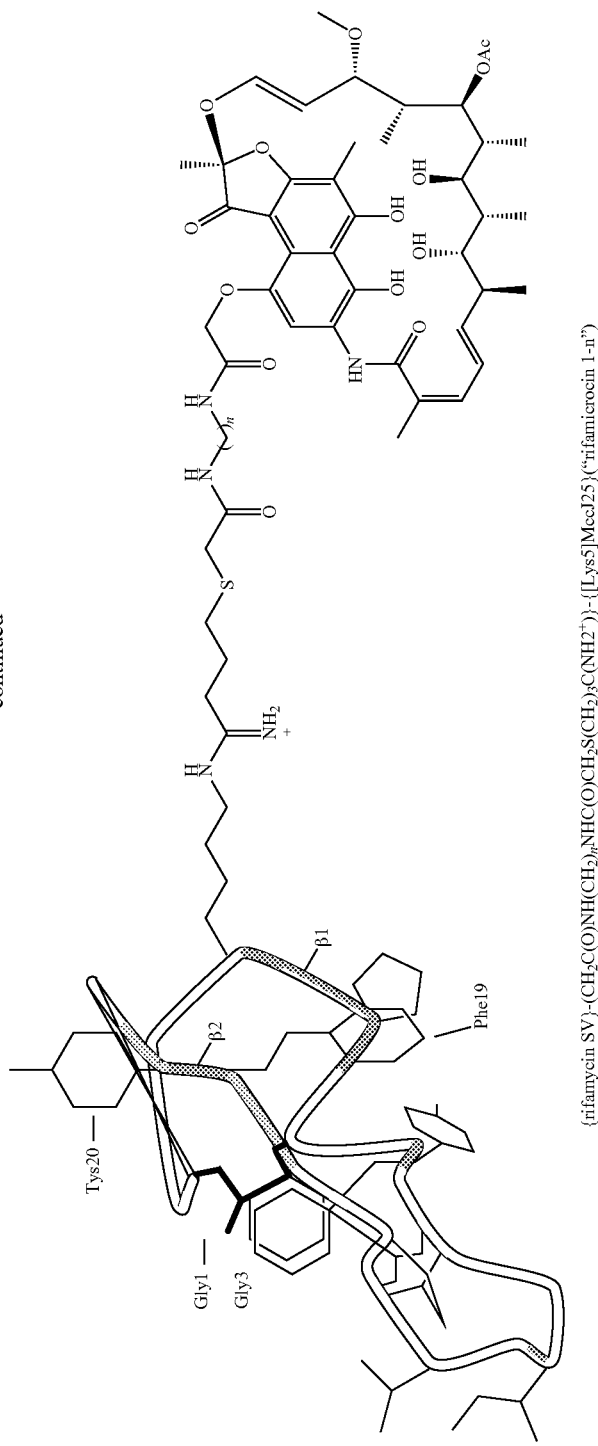

By way of further example, {rifamycin SV}—{CH$_2$C(O)NH(CH$_2$)$_n$NHC(O)(CH2)$_2$(C$_2$N$_3$)(CH$_2$)$_4$C(O)}-{[Lys5]microcin J25}, where n is an integer from about 2 to about 16 (referred to herein as "rifamicrocin 2-n"[rifamycin-microcin, linker type 2, linker variable n] can be prepared by reacting, under conditions that result in azide-alkyne [3+2]cycloaddition (see Rostovetsev, et al. (2002) *Angew. Chem. Int. Ed.* 41, 2596-2599 Wang, et al. (2003) *J. Amer. Chem. Soc.* 125, 3192-3193; Breibauer, et al. (2003) *ChemBioChem.* 4, 1147-1149): (1) {rifamycin SV}—{CH$_2$C(O)NH(CH$_2$)$_n$NHC(O)(CH$_2$)$_2$CCH, where n is an integer from about 2 to about 16; and (2) N$_3$(CH$_2$)$_4$C(O)-{[Lys5]microcin J25}.

By way of further example, {rifamycin SV}—{CH$_2$C(O)NH(CH$_2$)(C$_6$H$_3$)(O$^-$)C(O)NOH::(HO)B (C$_6$H$_4$)NHC(O)(CH$_2$)$_n$C(O)}-{[Lys5]microcin J25}, where n is an integer from about 2 to about 4 (referred to herein as "rifamicrocin 3-n" [rifamycin-microcin, linker type 3, linker variable n] can be prepared by reacting, under conditions that result in salicylhydroxamic-acid::phenylboronic-acid complex formation (see Stolowitz, et al. (2001) *Bioconj. Chem.* 12, 229-239; Wiley, et al. (2001), 12, 240-250): (1) {rifamycin SV}—CH$_2$C(O)NH(CH$_2$)(C$_6$H$_3$)(OH)C(O)NOH; and (2) (HO)$_2$B(C$_6$H$_4$)NHC(O)(CH$_2$)$_n$C(O)-{[Lys5]microcin J25}, where n is an integer from about 2 to about 4.

Pharmaceutical Preparations and Methods of Administration:

Identified compounds that inhibit bacterial replication can be administered to a patient at therapeutically effective doses to treat bacterial infection. A therapeutically effective dose refers to that amount of the compound sufficient to result in amelioration of symptoms of bacterial infection.

Toxicity and therapeutic efficacy of such compounds can be determined by standard pharmaceutical procedures in cell cultures or experimental animals for determining the LD$_{50}$ (the dose lethal to 50% of the population) and the ED$_{50}$ (the dose therapeutically effective in 50% of the population). The dose ratio between toxic and therapeutic effects is the therapeutic index and it can be expressed as the ratio LD$_{50}$/ED$_{50}$. Compounds that exhibit large therapeutic indices are preferred. While compounds that exhibit toxic side effects may be used, care should be taken to design a delivery system that targets such compounds to the site of infection in order to minimize damage to uninfected cells and reduce side effects.

The data obtained from the cell culture assays and animal studies can be used in formulating a range of dosage for use in humans. The dosage of such compounds lies preferably within a range of circulating concentrations that include the ED$_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC$_{50}$ (i.e., the concentration of the test compound which achieves a half-maximal infection, or a half-maximal inhibition) as determined in cell culture. Such information can be used to more accurately determine useful doses in humans. Levels in plasma may be measured, for example, by high performance liquid chromatography.

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). The tablets may be coated by methods well known in the alt. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

INDUSTRIAL APPLICABILITY

Compounds identified according to the target and method of this invention would have applications not only in antibacterial therapy, but also in: (a) identification of bacterial RNAP (diagnostics, environmental-monitoring, and sensors applications), (b) labeling of bacterial RNAP (diagnostics, environmental-monitoring, imaging, and sensors applications), (c) immobilization of bacterial RNAP (diagnostics, environmental-monitoring, and sensors applications), (d) purification of bacterial RNA polymerase (biotechnology applications), (e) regulation of bacterial gene expression (biotechnology applications), and (f) antisepsis (antiseptics, disinfectants, and advanced-materials applications).

EXAMPLES

With reference to the examples below, Applicant has identified compounds that inhibit bacterial RNAP.

Example 1

Synthesis of {Rifamycin SV}—{CH$_2$C(O)NH(CH$_2$)$_n$NHC(O)CH$_2$S(CH$_2$)$_3$C(NH$_2$$^+$)}-{[Lys5]MccJ25} ("Rifamicrocin 1-n"; n=6, 8, 10, or 12)

1.1: {Rifamycin SV}—CH$_2$C(O)NH(CH$_2$)$_n$NH$_2$ (n=6, 8, 10, or 12)

To rifamycin B (8 mg, 10.1 µmol; Pharmeks) in 150 µl anhydrous tetrahydrofuran, was added dicylohexylcarbodiimide (8 mg; 38.8 µmol; Aldrich) in 50 µl anhydrous tetrahydrofuran, the reaction mixture was incubated 15 min at 25° C., and 2 ml diethyl ether was added. The resulting precipitate was dissolved in 100 µl methanol containing $H_2N(CH_2)_nNH_2$ (10 mg; 80 µmol; Aldrich), where n=6, 8, 10, or 12, and the reaction mixture was incubated for 30 min at 25° C. The product was purified by thin-layer chromatography on silica gel in 2:1 (v/v) chloroform:ethanol, eluted from chromatographic plates in methanol, and dried in vacuo. Yield: 2.6 mg (3 µmol, 30% yield).

1.2: {Rifamycin SV}—$CH_2C(O)NH(CH_2)_nNHC(O)CH_2Br$ (n=6, 8, 10, or 12)

To {rifamycin SV}—$CH_2C(O)NH(CH_2)_nNH_2$, where n=6, 8, 10, or 12 (2.6 mg; 3 µmol; Example 1.1), in 150 µl anhydrous tetrahydrofuran, was added p-nitrophenylbromoacetate (7 mg; 27 µmol; Aldrich) in 50 µl anhydrous tetrahydrofuran and 3 µl diisopropylethylamine (2.2 mg; 17 µmol; Aldrich), and the reaction mixture was incubated 30 min at 25° C. The product was purified by thin-layer chromatography on silica gel in 3:1 (v/v) chloroform:ethanol, eluted from chromatographic plates in methanol, and further purified by high-pressure liquid chromatography (C8 column; buffer A=0.1% trifluoroacetic acid; buffer B=90% acetonitrile in 0.1% trifluoroacetic acid; gradient 50% B at 0 min, 100% B at 25 min). ($M^-$) for {rifamycin SV}—$CH_2C(O)NH(CH_2)_6N—HC(O)CH_2Br$: expected, 973.4; found, 972.6. ($M^-$) for {rifamycin SV}—$CH_2C(O)NH(CH_2)_8NHC(O)CH_2Br$: expected, 1000.4; found, 1000.4. (M) for {rifamycin SV}—$CH_2C(O)NH(CH_2)_{10}NHC(O)CH_2Br$: expected, 1028.4; found, 1029.4. ($M^-$) for {rifamycin SV}—$CH_2C(O)NH(CH_2)_{12}NHC(O)CH_2Br$: expected, 1056.4; found, 1056.5. Yield: 1 mg (1 µmol, 30% yield).

1.3: {Rifamycin SV}—$CH_2C(O)NH(CH_2)_nNHC(O)CH_3$ (n=12)

To {rifamycin SV}—$CH_2C(O)NH(CH_2)_nNH_2$, where n=12 (2.8 µg; 3 µmol; Example 1.1), in 150 µl anhydrous tetrahydrofuran, was added p-nitrophenylacetate (7 mg, 27 µmol; Aldrich) in 50 µl anhydrous tetrahydrofuran and 3 µl diisopropylethylamine (2.2 mg; 17 µmol; Aldrich) and the reaction mixture was incubated 30 min at 25° C. The product was purified by thin-layer chromatography on silica gel in 4:1 (v/v) chloroform:ethanol, eluted from chromatographic plates in methanol, and further purified by high-pressure liquid chromatography (C8 column; buffer A=0.1% trifluoroacetic acid; buffer B=90% acetonitrile in 0.1% trifluoroacetic acid; gradient=50% B at 0 min. 100% B at 25 min). Yield: 2.3 mg (2.4 µmol, 80% yield). ($M+H^+$) expected, 979.5; found, 980.6.

1.4: [Lys5]MccJ25

[Lys5]MccJ25 was prepared as described for MccJ25 in Mukhopadhyay et al., *Mol. Cell* 14:739-751, 2004, except that plasmid pTUC202-K5 was used in place of plasmid pTUC202. [Plasmid pTUC202 carries genes for synthesis and export of MccJ25 (Solbiati et al., *J. Bacteriol.* 181, 2659-2662, 1996). Plasmid pTUC202-K5, which carries genes for synthesis and export of [Lys13]MccJ25, was constructed from pTUC202 by use of site-directed mutagenesis (QuikChange Site-Directed Mutagenesis Kit; Stratagene).].

1.5: $HS(CH_2)_3C(NH_2^+)$-{[Lys5]MccJ25}

To [Lys5]MccJ25 (1 mg; 0.5 µmol; Example 1.4) in 200 µl 100 mM Tris-HCl, pH 8.0, was added iminothiolane (6.8 mg, 50 µmol; Aldrich) in 50 µl 100 mM Tris-HCl, pH 8.0, and the reaction mixture was incubated 6 h on ice. The product was purified by high-pressure liquid chromatography (C18 column; buffer A 0.1% trifluoroacetic acid; buffer B=90% acetonitrile in 0.1% trifluoroacetic acid; gradient=30% B at 0 min, 80% B at 30 min, 100% B at 35 min). ($M+H^+$): expected, 2200.1; found, 2201.6. Yield: 770 µg (0.35 µmol, 70% yield).

1.6: {Rifamycin SV}—$\{CH_2C(O)NH(CH_2)_nNHC(O)CH_2S(CH_2)_3C(NH_2^+)\}$-{[Lys5]MccJ25} ("Rifamicrocin 1-n"; n=6, 8, 10, or 12)

To $HS(CH_2)_3C(NH2^+)$-{[Lys5]MccJ25} (220 µg; 0.1 µmol; Example 1.5) in 50 µl 100 mM HEPES-OH, pH 8.0, was added {rifamycin SV}—$CH_2C(O)NH(CH_2)_nNHC(O)CH_2Br$, where n=6, 8, 10, or 12 (250 µg; 0.25 µmol; Example 1.2), in 50 µl DMF, and the reaction mixture was incubated 6 h on ice. The product was purified by high-pressure liquid chromatography (C18 column; buffer A=0.1% trifluoroacetic acid; buffer B: 90% acetonitrile in 0.1% trifluoroacetic acid; gradient=50% B at 0 min, 100% B at 25 min). ($M+H^+$) for rifamicrocin 1-6: expected, 3093.5; found, 3095.4. ($M+H^+$) for rifamicrocin 1-8: expected, 3121.6; found, 3125.5. ($M+Na^+$) for rifamicrocin 1-10: expected, 3172; found, 3173. ($M+H^+$) rifamicrocin 1-12: expected, 3177.6; found, 3181.7. Yield: 310 µg (0.1 µmol, 100 yield).

Example 2

Synthesis of {Rifamycin SV}—$\{CH_2C(O)NH(CH_2)_n(O)(CH_2)_2(C_2N_3)(CH_2)_4C(O)\}$-{[Lys5]MccJ25} ("Rifamicrocin 2-n"; n=10)

2.1: Ethyl 5-Azidovalerate

Ethyl 5-bromovalerate (2.1 g; 10 mmol; Aldrich) was added to a stirred suspension of sodium azide (1.3 g, 20 mmol; Fisher) in 5 ml dimethylformamide and 5 ml water, and the reaction mixture was heated 12 h at 80° Cs. The reaction was partitioned between diethyl ether (100 ml) and water (100 ml), and the resulting organic layer was washed with water (100 ml) and brine (100 ml), dried over sodium sulfate, and dried in vacuo. Yield: 1.6 g (9.3 mmol, 95% yield).

2.2: 5-Azidovaleric Acid

To ethyl 5-azidovalerate (1.6 g; 10 mmol; Example 2.1) in 5 ml-dimethylformamide, was added lithium hydroxide (1.0 g; 20 mmol; Fisher) in 5 ml water, and the reaction mixture was stirred 12 h at 25° C. The reaction mixture was adjusted to pH ~4 by addition of 1 N HCl and was extracted with 100 ml diethyl ether. The resulting organic layer was washed with water (100 ml) and brine (100 ml), dried over sodium sulfate, and dried in vacuo. Yield: 1.4 g (9.8 mmol, 99% yield).

2.3: Succinimidyl 5-Azidovalerate

To a suspension of 5-azidovaleric acid (715 mg; 5 mmol; Example 2.2) and N-hydroxysuccinimide (632 mg; 5.5 mmol; Aldrich) in 30 ml dichloromethane, was added 1-ethyl-3-(3-dimethylaminopropyl)carbodiimide hydrochloride (1.05 g; 5.5 mmol; Aldrich), and the reaction was stirred 12 h at room temperature. To the reaction mixture, was added water (50 ml), and the separated organic phase was washed with water (100 ml) and brine (100 ml), dried over sodium sulfate, dried in vacuo. The product was purified via flash chromatography on silica gel (240-400 mesh) in 3:1 (v/v) hexane:ethyl acetate. Yield: 843 mg (3.5 mmol, 70% yield). $M+H^+$: expected, 241.09.7; found, 241.03.

2.4: $N_3(CH_2)_4C(O)$-{[Lys5]MccJ25}

To [Lys5]MccJ25 (210 µg; 0.1 µmol; Example 1.4) in 100 µl dimethylsulfoxide, was added succinimidyl 5-azidovalerate (480 µg; 2 µmol; Example 2.3) and N,N'-diisopropylethylamine (1.5 mg; 12 µmol; Aldrich) in 1100 µL dimethylsulfoxide, and the reaction mixture was incubated 12 h at 4° C. The product was purified by high-pressure liquid chromatography (C18 column; buffer A=0.1% trifluoroacetic acid;

buffer B=90% acetonitrile in 0.1% trifluoroacetic acid; gradient=20% B at 0 min, 80% B at 30 min, 100% B at 35 min). (M+H$^+$): expected, 2221.1; found, 2219.6. Yield: 133 μg (0.06 μmol, 60% yield).

2.5: {Rifamycin SV}—CH$_2$C(O)NH(CH$_2$)$_n$NHC(O)CH$_2$CH$_2$CCH (n=10)

To {rifamycin SV}—CH$_2$C(O)NH(CH$_2$)$_{10}$NH$_2$, where n=10 (2.7 mg; 3 μmol; Example 1.1), in 250 μl anhydrous tetrahydrofuran, was added 4-pentynoic acid (3 mg, 30 μmol; Aldrich) in 50 μl anhydrous tetrahydrofuran, followed by 1-ethyl-3-(3-dimethylaminopropyl)carbodiimide hydrochloride (5.6 mg; 30 μmol; Aldrich) and 1-hydroxybenzotriazole (2.9 mg; 30 μmol; Aldrich) in 200 μl anhydrous tetrahydrofuran, and the reaction mixture was incubated 12 h at room temperature. The product was purified by high-pressure liquid chromatography (C8 column; buffer A=0.1% trifluoroacetic acid; buffer B=90% acetonitrile in 0.1% trifluoroacetic acid; gradient=50% B at 0 min, 100% B at 25 min). Yield: 2.4 mg (2.4 μmol, 80% yield). (M$^-$): expected, 988.5; found, 988.4.

2.6: {Rifamycin SV}—{CH$_2$C(O)NH(CH$_2$)$_n$NHC(O)(CH$_2$)$_2$(C$_2$N$_3$)(CH$_2$)$_4$C(O)}-{ounds on MccJ25} ("Rifamicrocin 2-n"; n=10)

To N$_3$(CH$_2$)$_4$C(O)-{[Lys5]MccJ25} (57.7 μg; 0.026 μmol; Example 2.4) in 100 μl water, was added {rifamycin SV}—CH$_2$C(O)NH(CH$_2$)$_n$NHC(O)CH$_2$CH$_2$CCH, where n=10 (43.5 μg; 0.044 μmol; Example 2.5) in 100 μl methanol, followed by 2 μl 50 mM copper sulfate and 2 μl 50 mM ascorbic acid, and the reaction mixture was incubated 12 h at room temperature. The product was purified by high-pressure liquid chromatography (C8 column; buffer A=0.1% trifluoroacetic acid; buffer B: 90% acetonitrile in 0.1% trifluoroacetic acid; gradient=50% B at 0 min, 100% B at 25 min). (M+H$^+$): expected, 3210.6; found, 3209.4.

Example 3

Measurement of Effects of Rifamicrocins on Transcription 3.1: RNAP

RNAP was prepared as described in Niu, et al. (1996) *Cell* 87, 1123-1134. [Asn516]β-RNAP, a strongly rifamycin-resistant RNAP derivative (see Jin, et al. (1988) *J. Mol. Biol.* 202, 45-58) was prepared in the same manner, except that plasmid pRL706-516N was used in place of plasmid pREII-NHα. [Plasmid pRL706-516N, which encodes C-terminally hexahistidine tagged [Asn516]β, was constructed from plasmid pRL706 (Severinov, et al. (1997) *J. Biol. Chem.* 272, 24137-24140) by use of site-directed mutagenesis (QuikChange Site-Directed Mutagenesis Kit; Stratagene).]

3.2: Transcription Assays

RNAP or [Asn516]β-RNAP (3 fmol; Example 3.1) and each test compound (250 fmol-100 pmol) were pre-equilibrated 30 min at 37° C. in 15 μl buffer A (50 mM Tris-HCl, pH 8.0, 100 mM KCl, 10 mM MgCl$_2$, 1 mM dithiothreitol, 10 ug/ml bovine serum albumin, and 5% glycerol). To the reaction mixture, was added 1 μl of 1 μM DNA fragment comprising positions -60 to +46 of the bacteriophage T5 N25 promoter (1 pmol; prepared as in Revyakin, et al. (2006) *Science*, in press), and, following incubation 15 min at 37° C., RNA synthesis was initiated by addition of 3 it of 6.7 mM ATP and 30 μM α[$^{32}$P]-UTP (0.6 Bq/fmol). Following 10 min at 37° C., the reaction was terminated by addition of 10/j 80% formamide, 10 mM EDTA, 0.04% bromophenol blue, and 0.04% xylene cyanol. Reaction products were heated 0 min at 90° C. and were analyzed by urea-PAGE (Sambrook, et al. (2001) *Molecular Cloning: A Laboratory Manual*, CSHL Press, Cold Spring Harbor, N.Y.), and quantified using a storage-phosphor scanner.

Rifamicrocins 1-6, 1-8, 1-10, and 1-12 (Example 1.6) were tested and were found potently to inhibit transcription, including transcription by a rifamycin-resistant RNAP derivative, [Asn516]β-RNAP. Rifamicrocins 1-6, 1-8, 1-10, and 1-12 were found to inhibit transcription by a rifamycin-resistant RNAP derivative, [Asn516]β-RNAP, with potencies approximately 10-25 times higher than that of the parent rifamycin, {rifamycin SV}—CH$_2$C(O)NH(CH$_2$)$_n$NHC(O)CH$_3$ (IC50=130 μM, 100 μM, 95 μM, and 48 μM, vs. IC50=1200 μM; FIG. 7). Furthermore, rifamicrocins 1-6, 1-8, 1-10, and 1-12 were found to inhibit transcription by a rifamycin-resistant RNAP derivative, [Asn516]β-RNAP, with potencies approximately 3-9 times higher than that of a prior-art rifamycin, rifamycin B (IC50=130 M, 100 μM, 95 μM, and 48 μM, vs. IC50=420 μM; FIG. 7).

Rifamicrocin 2-10 (Example 2.6) was tested and was found potently to inhibit transcription, including transcription by a rifamycin-resistant RNAP derivative, [Asn516]β-RNAP. Rifamicrocin 2-10 was found to inhibit transcription by a rifamycin-resistant RNAP derivative, [Asn516]β-RNAP, with a potency approximately 5 times higher than that of the parent rifamycin, {rifamycin SV}—CH$_2$C(O)NH(CH$_2$)$_n$NHC(O)CH$_2$CH$_2$CCH (IC50=220 μM vs. IC50=1100 μM; FIG. 8). Furthermore, rifamicrocin 2-10 was found to inhibit transcription by a rifamycin-resistant RNAP derivative, [Asn516]β-RNAP, with a potency approximately 2 times higher than that of a prior-art rifamycin, rifamycin B (IC50=220 μM vs. IC50=420 μM; FIG. 8).

Example 4

Measurement of Effects of Rifamicrocins on Bacterial Growth 4.1: Susceptibility Assays Aliquots (2.5 μl) of 1.56, 3.12, 6.25, 12.5, 25, 50, 100, 200, and 400 μM solutions of a test compound were spotted on plates containing *Escherichia coli* strain D21 f2/tolC (Fralick, et al. (1994) *J. Bacteriol.* 176, 6404-6406; ~10$^8$ cells) in LB top agar (Sambrook, et al. (2001) Sambrook, et al. (2001) *Molecular Cloning. A Laboratory Manual*, CSHL Press, Cold Spring Harbor, N.Y.; 3.5 ml) overlaid on LB agar (Sambrook, et al. (2001) Sambrook, et al. (2001) *Molecular Cloning: A Laboratory Manual*, CSHL Press, Cold Spring Harbor, N.Y.; 25 ml). Following incubation 12 h at 37° C., the lowest concentration of test compound resulting in detectable inhibition of bacterial growth was noted.

Rifamicrocin 1-10 (Example 1.6) was tested and was found potently to inhibit bacterial growth (detectable inhibition in assays with 12.5 μM solutions). Rifamicrocin 1-10 was found to inhibit bacterial growth with a potency ~4 times higher than the potency of a prior-art rifamycin, rifamycin SV (detectable inhibition in assays with 12.5 μM solutions vs. detectable inhibition in assays with 50 μM solutions).

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

All patent and non-patent publications cited in this specification are indicative of the level of skill of those skilled in the art to which this invention pertains. All these publications and patent applications are herein incorporated by reference to the same extent as if each individual publication or patent application were specifically and individually indicated to be incorporated herein by reference.

What is claimed is:

1. A compound having a structural formula (I):

X-α-Y     (I)

wherein X is an moiety that binds to the Rif pocket of a bacterial RNA polymerase and is selected from the group consisting of a rifamycin derivative, Y is a moiety that binds to the secondary channel of a bacterial RNA polymerase and is selected from the group consisting of a lariat peptide, a derivative of a lariat-peptide, tagetitoxin or ppGpp, and α is a linker, wherein said linker has a length of from about 15 Å to about 35 Å.

2. A compound according to claim 1, wherein said compound binds to a bacterial RNA polymerase.

3. A compound according to claim 2, wherein said compound binds to a bacterial RNA polymerase with an affinity higher than that of X and Y separately.

4. A compound according to claim 2, wherein said compound binds to a bacterial RNA polymerase resistant to at least one of X and Y.

5. A compound according to claim 1, wherein said compound inhibits a bacterial RNA polymerase.

6. A compound according to claim 5, wherein said compound inhibits a bacterial RNA polymerase with a potency higher than that of X and Y separately.

7. A compound according to claim 5, wherein said compound inhibits a bacterial RNA polymerase resistant to at least one of X and Y.

8. A compound according to claim 1, wherein X is a rifamycin derivative, and X is bonded to α through the rifamycin naphthol group.

9. A compound according to claim 8, wherein X is a rifamycin derivative, and X is bonded to a through at least one of the rifamycin O12 atom, the rifamycin C3 atom, and the rifamycin C4 atom.

10. A compound according to claim 9, wherein X is rifamycin SV, and X is bonded to a through the O12 atom of rifamycin SV.

11. A compound according to claim 1 wherein Y is a microcin J25 derivative.

12. A compound according to claim 1, wherein Y is a microcin J25 derivative, and Y is bonded to X through a microcin J25 residue 5.

13. A compound according to claim 12, wherein Y is a [Lys5]microcin J25, and Y is bonded to X through a Lys5 NZ atom of [Lys5]microcin J25.

14. A compound according to claim 1, wherein α contains a covalent bond.

15. A compound according to claim 1, wherein α contains a coordinate-covalent bond.

16. A compound according to claim 1, wherein α contains a non-covalent bond.

17. A compound according to claim 1, wherein said compound is prepared from precursors X-α' and 'α-Y, wherein α' and 'α are moieties that can react to form α.

18. A compound according to claim 17, wherein said compound is prepared from precursors X-α' and 'α-Y in the presence of a bacterial RNA polymerase.

19. A compound according to claim 17, wherein said compound is prepared from precursors X-α' and 'α-Y in the presence of a bacterial RNA polymerase, said bacterial RNA polymerase serving as a template for reaction of X-α' and 'α-Y.

20. A compound according to claim 1, having the general formula {rifamycin SV}-{$CH_2C(O)NH(CH_2)_n NHC(O)CH_2S (CH_2)_3C(NH_2^+)$}-{[Lys5]microcin J25}, where n is an integer from about 4 to about 18.

21. A compound according to claim 1, having the general formula {rifamycin SV}-{$CH_2C(O)NH(CH_2)_n NHC(O)CH_2S(H_2)_3C(NH_2^+)$}-{[Lys5]microcin J25}, where n is an integer from about 6 to about 16.

22. A compound according to claim 21, where n=12.

23. A compound according to claim 1, having the general formula {rifamycin SV}-{$CH_2C(O)NH(CH_2)_n NHC(O)(CH2)_2(C_2N_3)(CH_2)_4C(O)$}-{[Lys5]microcin J25}, where n is an integer from about 2 to about 16.

24. A compound according to claim 1, having the general formula {rifamycin SV}-{$CH_2C(O)NH(CH_2)_n NHC(O)(CH2)_2(C_2N_3)(CH_2)_4C(O)$}-{[Lys5]microcin J25}, where n is an integer from about 4 to about 14.

25. A compound according to claim 24, where n=10.

26. A method of preparing a compound according to claim 1, said method comprising:
providing precursors X-α' and 'α-Y, and
reacting the α' moiety of X-α' and the 'α moiety of 'α-Y to form X-α-Y.

27. A method according to claim 26, wherein one precursor contains an activated ester and the other precursor contains an amine.

28. A method according to claim 26, wherein one precursor contains a haloacetyl moiety and the other precursor contains an amine.

29. A method according to claim 26, wherein one precursor contains a haloacetyl moiety and the other precursor contains a sulfhydryl.

30. A method according is claim 26, wherein one precursor contains an azide and the other precursor contains an alkyne.

31. A method according to claim 26, wherein one precursor contains an azide and the other precursor contains a phosphine.

32. A method according to claim 26, wherein one precursor contains a boronic acid and the other precursor contains a substituted phenol.

33. A method according to claim 26, wherein one precursor contains phenylboronic acid and the other precursor contains salicylhydroxamic acid.

34. A method according to claim 26, wherein moieties .alpha.' and '.alpha. of precursors X-.alpha.' and '.alpha.-Y react in the presence of a bacterial RNA polymerase.

35. A method according to claim 34, wherein the bacterial RNA polymerase serves as a template for reaction of X-.alpha.' and '.alpha.-Y.

36. A method of preparing a bipartite inhibitor of bacterial RNA polymerase, said method comprising reacting {rifamycin SV}-{$CH_2C(O)NH(CH_2)_n NHC(O)CH_2Z$, where n is an integer from about 4 to about 18, and is a halogen, with $HS(CH_2)_3C(NH_2^+)$}-{[Lys5]microcin J25}.

37. A method of using compound according to claim 1 to bind to a bacterial RNA polymerase.

38. A method of using compound according to claim 1 to inhibit a bacterial RNA polymerase.

39. A method of using compound according to claim 1 to inhibit bacterial gene expression.

40. A method of using the compound according to claim 1 to inhibit bacterial growth.

41. A method of using the compound according to claim 1 to treat bacterial infection.

42. A pharmaceutical preparation comprising a compound according to claim 1 and a physiologically acceptable carrier or excipient.

* * * * *

```
                        SEQUENCE LISTING

<160> NUMBER OF SEQ ID NOS: 69

<210> SEQ ID NO 1
<211> LENGTH: 6
<212> TYPE: PRT
<213> ORGANISM: Escherichia coli

<400> SEQUENCE: 1

Glu Arg Val Ile Val Ser
1               5

<210> SEQ ID NO 2
<211> LENGTH: 6
<212> TYPE: PRT
<213> ORGANISM: Haemophilus influenzae

<400> SEQUENCE: 2

Glu Arg Val Ile Val Ser
1               5

<210> SEQ ID NO 3
<211> LENGTH: 6
<212> TYPE: PRT
<213> ORGANISM: Vibrio cholerae

<400> SEQUENCE: 3

Glu Arg Val Ile Val Ser
1               5

<210> SEQ ID NO 4
<211> LENGTH: 6
<212> TYPE: PRT
<213> ORGANISM: Pseudomonas aeruginosa

<400> SEQUENCE: 4

Glu Arg Val Ile Val Ser
1               5

<210> SEQ ID NO 5
<211> LENGTH: 6
<212> TYPE: PRT
<213> ORGANISM: Treponema pallidum

<400> SEQUENCE: 5

Glu Arg Val Val Val Ser
1               5

<210> SEQ ID NO 6
<211> LENGTH: 6
<212> TYPE: PRT
<213> ORGANISM: Borrelia burgdorferi

<400> SEQUENCE: 6

Glu Arg Val Val Val Ser
1               5

<210> SEQ ID NO 7
<211> LENGTH: 6
```

```
<212> TYPE: PRT
<213> ORGANISM: Xylella fastidiosa

<400> SEQUENCE: 7

Glu Arg Val Ile Val Ser
1               5

<210> SEQ ID NO 8
<211> LENGTH: 6
<212> TYPE: PRT
<213> ORGANISM: Campylobacter jejuni

<400> SEQUENCE: 8

Glu Arg Val Val Val Asn
1               5

<210> SEQ ID NO 9
<211> LENGTH: 6
<212> TYPE: PRT
<213> ORGANISM: Neisseria meningitidis

<400> SEQUENCE: 9

Glu Arg Val Ile Val Ser
1               5

<210> SEQ ID NO 10
<211> LENGTH: 6
<212> TYPE: PRT
<213> ORGANISM: Rickettsia prowazekii

<400> SEQUENCE: 10

Glu Arg Val Val Val Ser
1               5

<210> SEQ ID NO 11
<211> LENGTH: 6
<212> TYPE: PRT
<213> ORGANISM: Chlamydia trachomatis

<400> SEQUENCE: 11

Glu Arg Val Val Val Ser
1               5

<210> SEQ ID NO 12
<211> LENGTH: 6
<212> TYPE: PRT
<213> ORGANISM: Mycoplasma pneumoniae

<400> SEQUENCE: 12

Glu Lys Phe Val Ile Ala
1               5

<210> SEQ ID NO 13
<211> LENGTH: 6
<212> TYPE: PRT
<213> ORGANISM: Bacillus subtilis

<400> SEQUENCE: 13

Glu Arg Val Ile Val Ser
1               5

<210> SEQ ID NO 14
<211> LENGTH: 6
<212> TYPE: PRT
<213> ORGANISM: Staphylococcus aureus
```

```
<400> SEQUENCE: 14

Glu Arg Val Ile Val Ser
1               5

<210> SEQ ID NO 15
<211> LENGTH: 6
<212> TYPE: PRT
<213> ORGANISM: Mycobacterium tuberculosis

<400> SEQUENCE: 15

Glu Arg Val Val Val Ser
1               5

<210> SEQ ID NO 16
<211> LENGTH: 6
<212> TYPE: PRT
<213> ORGANISM: Synechocystis sp.

<400> SEQUENCE: 16

Glu Arg Val Ile Val Asn
1               5

<210> SEQ ID NO 17
<211> LENGTH: 6
<212> TYPE: PRT
<213> ORGANISM: Aquifex aeolicus

<400> SEQUENCE: 17

Glu Arg Ile Ile Ile Asn
1               5

<210> SEQ ID NO 18
<211> LENGTH: 6
<212> TYPE: PRT
<213> ORGANISM: Deinococcus radiodurans

<400> SEQUENCE: 18

Asp Arg Val Val Ile Ser
1               5

<210> SEQ ID NO 19
<211> LENGTH: 6
<212> TYPE: PRT
<213> ORGANISM: Thermus thermophilus

<400> SEQUENCE: 19

Asp Arg Val Ile Val Ser
1               5

<210> SEQ ID NO 20
<211> LENGTH: 6
<212> TYPE: PRT
<213> ORGANISM: Thermus aquaticus

<400> SEQUENCE: 20

Asp Arg Val Ile Val Ser
1               5

<210> SEQ ID NO 21
<211> LENGTH: 6
<212> TYPE: PRT
<213> ORGANISM: Homo sapiens

<400> SEQUENCE: 21

Glu Lys Val Ile Arg Met
```

<210> SEQ ID NO 22
<211> LENGTH: 6
<212> TYPE: PRT
<213> ORGANISM: Homo sapiens

<400> SEQUENCE: 22

Glu Lys Val Leu Ile Ala
1               5

<210> SEQ ID NO 23
<211> LENGTH: 6
<212> TYPE: PRT
<213> ORGANISM: Homo sapiens

<400> SEQUENCE: 23

Glu Lys Val Ile Leu Ile
1               5

<210> SEQ ID NO 24
<211> LENGTH: 65
<212> TYPE: PRT
<213> ORGANISM: Escherichia coli

<400> SEQUENCE: 24

Ser Gln Leu Ser Gln Phe Met Asp Gln Asn Asn Pro Leu Ser Glu Ile
1               5                   10                  15

Thr His Lys Arg Arg Ile Ser Ala Leu Gly Pro Gly Gly Leu Thr Arg
            20                  25                  30

Glu Arg Ala Gly Phe Glu Val Arg Asp Val His Pro Thr His Tyr Gly
        35                  40                  45

Arg Val Cys Pro Ile Glu Thr Pro Glu Gly Pro Asn Ile Gly Leu Ile
    50                  55                  60

Asn
65

<210> SEQ ID NO 25
<211> LENGTH: 65
<212> TYPE: PRT
<213> ORGANISM: Haemophilus influenzae

<400> SEQUENCE: 25

Ser Gln Leu Ser Gln Phe Met Asp Gln Asn Asn Pro Leu Ser Glu Val
1               5                   10                  15

Thr His Lys Arg Arg Ile Ser Ala Leu Gly Pro Gly Gly Leu Thr Arg
            20                  25                  30

Glu Arg Ala Gly Phe Glu Val Arg Asp Val His Asn Thr His Tyr Gly
        35                  40                  45

Arg Leu Cys Pro Ile Glu Thr Pro Glu Gly Pro Asn Ile Gly Leu Ile
    50                  55                  60

Asn
65

<210> SEQ ID NO 26
<211> LENGTH: 65
<212> TYPE: PRT
<213> ORGANISM: Vibrio cholerae

<400> SEQUENCE: 26

Ser Gln Leu Ser Gln Phe Met Asp Gln Asn Asn Pro Leu Ser Glu Val
1               5                   10                  15

```
Thr His Lys Arg Arg Ile Ser Ala Leu Gly Pro Gly Gly Leu Thr Arg
         20                  25                  30

Glu Arg Ala Gly Phe Glu Val Arg Asp Val His Asn Thr His Tyr Gly
         35                  40                  45

Arg Leu Cys Pro Ile Glu Thr Pro Glu Gly Pro Asn Ile Gly Leu Ile
     50                  55                  60

Asn
65

<210> SEQ ID NO 27
<211> LENGTH: 65
<212> TYPE: PRT
<213> ORGANISM: Pseudomonas aeruginosa

<400> SEQUENCE: 27

Ser Gln Leu Ser Gln Phe Met Asp Gln Asn Asn Pro Leu Ser Glu Thr
1               5                   10                  15

Thr His Lys Arg Arg Val Ser Ala Leu Gly Pro Gly Gly Leu Thr Arg
         20                  25                  30

Glu Arg Ala Gly Phe Glu Val Arg Asp Val His Pro Thr His Tyr Gly
         35                  40                  45

Arg Val Cys Pro Ile Glu Thr Pro Glu Gly Pro Asn Ile Gly Leu Ile
     50                  55                  60

Asn
65

<210> SEQ ID NO 28
<211> LENGTH: 65
<212> TYPE: PRT
<213> ORGANISM: Treponema pallidum

<400> SEQUENCE: 28

Ser Gln Leu Ser Gln Phe Met Asp Gln Val Asn Pro Leu Ala Glu Leu
1               5                   10                  15

Thr His Lys Arg Arg Ile Asn Ala Leu Gly Pro Gly Gly Leu Ser Arg
         20                  25                  30

Glu Arg Ala Gly Phe Glu Val Arg Asp Val His Asn Thr His Tyr Gly
         35                  40                  45

Arg Leu Cys Pro Ile Glu Thr Pro Glu Gly Pro Asn Ile Gly Leu Ile
     50                  55                  60

Val
65

<210> SEQ ID NO 29
<211> LENGTH: 65
<212> TYPE: PRT
<213> ORGANISM: Borrelia burgdorferi

<400> SEQUENCE: 29

Ser Gln Leu Ser Gln Phe Met Asp Gln Val Asn Pro Leu Ala Glu Leu
1               5                   10                  15

Thr His Lys Arg Arg Leu Asn Ala Leu Gly Pro Gly Gly Leu Ser Arg
         20                  25                  30

Asp Arg Ala Gly Phe Glu Val Arg Asp Val His Tyr Thr His Tyr Gly
         35                  40                  45

Arg Met Cys Pro Ile Glu Thr Pro Glu Gly Pro Asn Ile Gly Leu Ile
     50                  55                  60

Val
```

<210> SEQ ID NO 30
<211> LENGTH: 65
<212> TYPE: PRT
<213> ORGANISM: Xylella fastidiosa

<400> SEQUENCE: 30

Ser Gln Leu Ser Gln Phe Met Asp Gln Asn Asn Pro Leu Ser Glu Val
1 5 10 15

Thr His Lys Arg Arg Leu Ser Ala Leu Gly Pro Gly Gly Leu Thr Arg
20 25 30

Glu Arg Ala Gly Phe Glu Val Arg Asp Val His Leu Ser His Tyr Gly
35 40 45

Cys Leu Cys Thr Ile Glu Thr Pro Glu Gly Pro Asn Ile Gly Leu Ile
50 55 60

Asn
65

<210> SEQ ID NO 31
<211> LENGTH: 65
<212> TYPE: PRT
<213> ORGANISM: Campylobacter jejuni

<400> SEQUENCE: 31

Gly Gln Leu Ser Gln Phe Met Asp Gln Thr Asn Pro Leu Ser Glu Val
1 5 10 15

Thr His Lys Arg Arg Leu Ser Ala Leu Gly Glu Gly Gly Leu Val Lys
20 25 30

Glu Arg Ala Gly Phe Glu Val Arg Asp Val His Ala Thr His Tyr Gly
35 40 45

Arg Leu Cys Pro Val Glu Thr Pro Glu Gly Gln Asn Ile Gly Leu Ile
50 55 60

Asn
65

<210> SEQ ID NO 32
<211> LENGTH: 65
<212> TYPE: PRT
<213> ORGANISM: Neisseria meningitidis

<400> SEQUENCE: 32

Ser Gln Leu Ser Gln Phe Met Asp Gln Thr Asn Pro Leu Ser Glu Val
1 5 10 15

Thr His Lys Arg Arg Val Ser Ala Leu Gly Pro Gly Gly Leu Thr Arg
20 25 30

Glu Arg Ala Gly Phe Glu Val Arg Asp Val His Pro Thr His Tyr Gly
35 40 45

Arg Met Cys Pro Ile Glu Thr Pro Glu Gly Pro Asn Ile Gly Leu Ile
50 55 60

Asn
65

<210> SEQ ID NO 33
<211> LENGTH: 65
<212> TYPE: PRT
<213> ORGANISM: Rickettsia prowazekii

<400> SEQUENCE: 33

Ser Gln Leu Ser Gln Phe Met Asp Gln Thr Asn Pro Leu Ser Glu Ile

```
                1               5                   10                  15
Thr His Lys Arg Arg Leu Ser Ala Leu Gly Pro Gly Gly Leu Ser Arg
                20                  25                  30

Asp Arg Ala Gly Phe Glu Val Arg Asp Val His Pro Thr His Tyr Gly
                35                  40                  45

Arg Ile Cys Pro Ile Glu Thr Pro Glu Gly Gln Asn Ile Gly Leu Ile
        50                  55                  60

Asn
65

<210> SEQ ID NO 34
<211> LENGTH: 65
<212> TYPE: PRT
<213> ORGANISM: Chlamydia trachomatis

<400> SEQUENCE: 34

Ser Gln Leu Ser Gln Phe Met Asp Gln Thr Asn Pro Val Ala Glu Leu
1               5                   10                  15

Thr His Lys Arg Arg Leu Ser Ala Leu Gly Pro Gly Gly Leu Asn Arg
                20                  25                  30

Glu Arg Ala Gly Phe Glu Val Arg Asp Val His Ala Ser His Tyr Gly
                35                  40                  45

Arg Leu Cys Pro Ile Glu Thr Pro Glu Gly Pro Asn Ile Gly Leu Ile
        50                  55                  60

Thr
65

<210> SEQ ID NO 35
<211> LENGTH: 65
<212> TYPE: PRT
<213> ORGANISM: Mycoplasma pneumoniae

<400> SEQUENCE: 35

His Gln Leu Thr Gln Phe Leu Asp His Gln Asn Pro Leu Ser Glu Leu
1               5                   10                  15

Ser Asn Lys Arg Arg Ile Ser Ala Met Gly Pro Gly Gly Ile Ser Arg
                20                  25                  30

Glu Asp Pro Asn Leu Asp Ile Arg Asp Val His Tyr Ser Gln Tyr Gly
                35                  40                  45

Arg Ile Cys Pro Ile Glu Thr Pro Glu Gly Met Asn Ile Gly Leu Ile
        50                  55                  60

Met
65

<210> SEQ ID NO 36
<211> LENGTH: 65
<212> TYPE: PRT
<213> ORGANISM: Bacillus subtilis

<400> SEQUENCE: 36

Ser Gln Leu Ser Gln Phe Met Asp Gln Thr Asn Pro Leu Ala Glu Leu
1               5                   10                  15

Thr His Lys Arg Arg Leu Ser Ala Leu Gly Pro Gly Gly Leu Thr Arg
                20                  25                  30

Glu Arg Ala Gly Met Glu Val Arg Asp Val His Tyr Ser His Tyr Gly
                35                  40                  45

Arg Met Cys Pro Ile Glu Thr Pro Glu Gly Pro Asn Ile Gly Leu Ile
        50                  55                  60
```

-continued

Asn
65

<210> SEQ ID NO 37
<211> LENGTH: 65
<212> TYPE: PRT
<213> ORGANISM: Staphylococcus aureus

<400> SEQUENCE: 37

Ser Gln Leu Ser Gln Phe Met Asp Gln Ala Asn Pro Leu Ala Glu Leu
1               5                   10                  15

Thr His Lys Arg Arg Leu Ser Ala Leu Gly Pro Gly Gly Leu Thr Arg
            20                  25                  30

Glu Arg Ala Gln Met Glu Val Arg Asp Val His Tyr Ser His Tyr Gly
        35                  40                  45

Arg Met Cys Pro Ile Glu Thr Pro Glu Gly Pro Asn Ile Gly Leu Ile
    50                  55                  60

Asn
65

<210> SEQ ID NO 38
<211> LENGTH: 65
<212> TYPE: PRT
<213> ORGANISM: Mycobacterium tuberculosis

<400> SEQUENCE: 38

Ser Gln Leu Ser Gln Phe Met Asp Gln Asn Asn Pro Leu Ser Gly Leu
1               5                   10                  15

Thr His Lys Arg Arg Leu Ser Ala Leu Gly Pro Gly Gly Leu Ser Arg
            20                  25                  30

Glu Arg Ala Gly Leu Glu Val Arg Asp Val His Pro Ser His Tyr Gly
        35                  40                  45

Arg Met Cys Pro Ile Glu Thr Pro Glu Gly Pro Asn Ile Gly Leu Ile
    50                  55                  60

Gly
65

<210> SEQ ID NO 39
<211> LENGTH: 65
<212> TYPE: PRT
<213> ORGANISM: Synechocystis sp.

<400> SEQUENCE: 39

Ser Gln Leu Ser Gln Phe Met Asp Gln Thr Asn Pro Leu Ala Glu Leu
1               5                   10                  15

Thr His Lys Arg Arg Ile Ser Ala Leu Gly Pro Gly Gly Leu Thr Arg
            20                  25                  30

Glu Arg Ala Gly Phe Ala Val Arg Asp Ile His Pro Ser His His Gly
        35                  40                  45

Arg Ile Cys Pro Val Glu Thr Pro Glu Gly Pro Asn Ala Gly Leu Ile
    50                  55                  60

Gly
65

<210> SEQ ID NO 40
<211> LENGTH: 65
<212> TYPE: PRT
<213> ORGANISM: Aquifex aeolicus

<400> SEQUENCE: 40

```
Gly Gln Leu Ser Gln Tyr Leu Asp Asn Thr Asn Pro Leu Ser Glu Leu
1               5                   10                  15

Thr His Lys Arg Arg Leu Ser Ala Leu Gly Pro Gly Gly Leu Thr Arg
            20                  25                  30

Glu Ser Ala Lys Phe Glu Ile Arg Asp Val His Pro Ser His Tyr Gly
        35                  40                  45

Arg Ile Cys Pro Ile Glu Thr Pro Glu Gly Gln Asn Ile Gly Leu Val
    50                  55                  60

Thr
65

<210> SEQ ID NO 41
<211> LENGTH: 65
<212> TYPE: PRT
<213> ORGANISM: Deinococcus radiodurans

<400> SEQUENCE: 41

Ser Gln Leu Ser Gln Phe Lys Asp Gln Thr Asn Pro Leu Ser Asp Leu
1               5                   10                  15

Arg His Lys Arg Arg Ile Ser Ala Leu Gly Pro Gly Gly Leu Thr Arg
            20                  25                  30

Glu Arg Ala Gly Phe Asp Val Arg Asp Val His Arg Thr His Tyr Gly
        35                  40                  45

Arg Ile Cys Pro Ile Glu Thr Pro Glu Gly Ala Asn Ile Gly Leu Ile
    50                  55                  60

Ser
65

<210> SEQ ID NO 42
<211> LENGTH: 65
<212> TYPE: PRT
<213> ORGANISM: Thermus thermophilus

<400> SEQUENCE: 42

Ser Gln Leu Ser Gln Phe Lys Asp Glu Thr Asn Pro Leu Ser Ser Leu
1               5                   10                  15

Arg His Lys Arg Arg Ile Ser Ala Leu Gly Pro Gly Gly Leu Thr Arg
            20                  25                  30

Glu Arg Ala Gly Phe Asp Val Arg Asp Val His Arg Thr His Tyr Gly
        35                  40                  45

Arg Ile Cys Pro Val Glu Thr Pro Glu Gly Ala Asn Ile Gly Leu Ile
    50                  55                  60

Thr
65

<210> SEQ ID NO 43
<211> LENGTH: 65
<212> TYPE: PRT
<213> ORGANISM: Thermus aquaticus

<400> SEQUENCE: 43

Ser Gln Leu Ser Gln Phe Lys Asp Glu Thr Asn Pro Leu Ser Ser Leu
1               5                   10                  15

Arg His Lys Arg Arg Ile Ser Ala Leu Gly Pro Gly Gly Leu Thr Arg
            20                  25                  30

Glu Arg Ala Gly Phe Asp Val Arg Asp Val His Arg Thr His Tyr Gly
        35                  40                  45

Arg Ile Cys Pro Val Glu Thr Pro Glu Gly Ala Asn Ile Gly Leu Ile
    50                  55                  60
```

```
Thr
 65

<210> SEQ ID NO 44
<211> LENGTH: 63
<212> TYPE: PRT
<213> ORGANISM: Homo sapiens

<400> SEQUENCE: 44

Asp Ser Gly Leu Cys Val Val Ala Asp Lys Leu Asn Phe Ile Arg Tyr
 1               5                   10                  15

Leu Ser His Phe Arg Cys Val His Arg Gly Ala Asp Phe Ala Lys Met
                20                  25                  30

Arg Thr Thr Thr Val Arg Arg Leu Leu Pro Glu Ser Trp Gly Phe Leu
            35                  40                  45

Cys Pro Val His Thr Pro Asp Gly Glu Pro Cys Gly Leu Met Asn
        50                  55                  60

<210> SEQ ID NO 45
<211> LENGTH: 61
<212> TYPE: PRT
<213> ORGANISM: Homo sapiens

<400> SEQUENCE: 45

Ala Gly Val Ser Gln Val Leu Asn Arg Leu Thr Phe Ala Ser Thr Leu
 1               5                   10                  15

Ser His Leu Arg Arg Leu Asn Ser Pro Ile Gly Arg Asp Gly Lys Leu
                20                  25                  30

Ala Lys Pro Arg Gln Leu His Asn Thr Leu Trp Gly Met Val Cys Pro
            35                  40                  45

Ala Glu Thr Pro Glu Gly His Ala Val Gly Leu Val Lys
        50                  55                  60

<210> SEQ ID NO 46
<211> LENGTH: 62
<212> TYPE: PRT
<213> ORGANISM: Homo sapiens

<400> SEQUENCE: 46

Arg Gln Gly Val Thr Gln Val Leu Ser Arg Leu Ser Tyr Ile Ser Ala
 1               5                   10                  15

Leu Gly Met Met Thr Arg Ile Ser Ser Gln Phe Glu Lys Thr Arg Lys
                20                  25                  30

Val Ser Gly Pro Arg Ser Leu Gln Pro Ser Gln Trp Gly Met Leu Cys
            35                  40                  45

Pro Ser Asp Thr Pro Glu Gly Glu Ala Cys Gly Leu Val Lys
        50                  55                  60

<210> SEQ ID NO 47
<211> LENGTH: 76
<212> TYPE: PRT
<213> ORGANISM: Escherichia coli

<400> SEQUENCE: 47

Met Ala Asp Ser Gly Ala Arg Gly Ser Ala Gln Ile Arg Gln Leu
 1               5                   10                  15

Ala Gly Met Arg Gly Leu Met Ala Lys Pro Asp Gly Ser Ile Ile Glu
                20                  25                  30

Thr Pro Ile Thr Ala Asn Phe Arg Glu Gly Leu Asn Val Leu Gln Tyr
            35                  40                  45
```

```
Phe Ile Ser Thr His Gly Ala Arg Lys Gly Leu Ala Asp Thr Ala Leu
        50                  55                  60

Lys Thr Ala Asn Ser Gly Tyr Leu Thr Arg Arg Leu
 65                  70                  75
```

<210> SEQ ID NO 48
<211> LENGTH: 76
<212> TYPE: PRT
<213> ORGANISM: Haemophilus influenzae

<400> SEQUENCE: 48

```
Met Ala Asp Ser Gly Ala Arg Gly Ser Ala Ala Gln Ile Arg Gln Leu
 1               5                  10                  15

Ala Gly Met Arg Gly Leu Met Ala Arg Pro Asp Gly Ser Ile Ile Glu
            20                  25                  30

Thr Pro Ile Thr Ala Asn Phe Arg Glu Gly Leu Asn Val Leu Gln Tyr
        35                  40                  45

Phe Ile Ser Thr His Gly Ala Arg Lys Gly Leu Ala Asp Thr Ala Leu
        50                  55                  60

Lys Thr Ala Asn Ser Gly Tyr Leu Thr Arg Arg Leu
 65                  70                  75
```

<210> SEQ ID NO 49
<211> LENGTH: 76
<212> TYPE: PRT
<213> ORGANISM: Vibrio cholerae

<400> SEQUENCE: 49

```
Met Ala Asp Ser Gly Ala Arg Gly Ser Ala Ala Gln Ile Arg Gln Leu
 1               5                  10                  15

Ala Gly Met Arg Gly Leu Met Ala Arg Pro Asp Gly Ser Ile Ile Glu
            20                  25                  30

Thr Pro Ile Thr Ala Asn Phe Arg Glu Gly Leu Asn Val Leu Gln Tyr
        35                  40                  45

Phe Ile Ser Thr His Gly Ala Arg Lys Gly Leu Ala Asp Thr Ala Leu
        50                  55                  60

Lys Thr Ala Asn Ser Gly Tyr Leu Thr Arg Arg Leu
 65                  70                  75
```

<210> SEQ ID NO 50
<211> LENGTH: 76
<212> TYPE: PRT
<213> ORGANISM: Pseudomonas aeruginosa

<400> SEQUENCE: 50

```
Met Ala Asp Ser Gly Ala Arg Gly Ser Ala Ala Gln Ile Arg Gln Leu
 1               5                  10                  15

Ala Gly Met Arg Gly Leu Met Ala Lys Pro Asp Gly Ser Ile Ile Glu
            20                  25                  30

Thr Pro Ile Thr Ala Asn Phe Arg Glu Gly Leu Asn Val Leu Gln Tyr
        35                  40                  45

Phe Ile Ser Thr His Gly Ala Arg Lys Gly Leu Ala Asp Thr Ala Leu
        50                  55                  60

Lys Thr Ala Asn Ser Gly Tyr Leu Thr Arg Arg Leu
 65                  70                  75
```

<210> SEQ ID NO 51
<211> LENGTH: 76
<212> TYPE: PRT

<213> ORGANISM: Treponema pallidum

<400> SEQUENCE: 51

Met Ala Thr Ser Gly Ala Arg Gly Ser Ala 35                  40                  45
Phe Ile Ser Thr His Gly Ala Arg Lys Gly Leu Ala Asp Thr Ala Leu
    50                  55                  60

Lys Thr Ala Asn Ala Gly Tyr Leu Thr Arg Lys Leu
65                  70                  75

<210> SEQ ID NO 55
<211> LENGTH: 76
<212> TYPE: PRT
<213> ORGANISM: Neisseria meningitidis

<400> SEQUENCE: 55

Met Ala Asp Ser Gly Ala Arg Gly Ser Ala Gln Ile Lys Gln Leu
1               5                   10                  15

Ser Gly Met Arg Gly Leu Met Ala Lys Pro Asp Gly Ser Ile Ile Glu
                20                  25                  30

Thr Pro Ile Thr Ser Asn Phe Arg Glu Gly Leu Thr Val Leu Gln Tyr
            35                  40                  45

Phe Ile Ala Thr His Gly Ala Arg Lys Gly Leu Ala Asp Thr Ala Leu
    50                  55                  60

Lys Thr Ala Asn Ser Gly Tyr Leu Thr Arg Arg Leu
65                  70                  75

<210> SEQ ID NO 56
<211> LENGTH: 76
<212> TYPE: PRT
<213> ORGANISM: Rickettsia prowazekii

<400> SEQUENCE: 56

Met Ala Ile Ser Gly Ala Arg Gly Ser Phe Gln Gln Ile Lys Gln Leu
1               5                   10                  15

Gly Gly Met Arg Gly Leu Met Thr Lys Ser Asn Gly Gln Ile Ile Gln
                20                  25                  30

Thr Pro Ile Thr Ser Asn Phe Lys Glu Gly Leu Thr Glu Phe Glu Cys
            35                  40                  45

Phe Asn Ser Ala Asn Gly Met Arg Lys Gly Gln Ile Asp Thr Ala Leu
    50                  55                  60

Lys Thr Ala Ser Ser Gly Tyr Leu Thr Arg Lys Leu
65                  70                  75

<210> SEQ ID NO 57
<211> LENGTH: 76
<212> TYPE: PRT
<213> ORGANISM: Chlamydia trachomatis

<400> SEQUENCE: 57

Met Ala Asp Ser Gly Ala Arg Gly Asn Lys Ser Gln Leu Lys Gln Leu
1               5                   10                  15

Gly Ala Leu Arg Gly Leu Met Ala Lys Pro Asn Gly Ala Ile Ile Glu
                20                  25                  30

Ser Pro Ile Thr Ser Asn Phe Arg Glu Gly Leu Thr Val Leu Glu Tyr
            35                  40                  45

Ser Ile Ser Ser His Gly Ala Pro Lys Gly Leu Ala Asp Thr Ala Leu
    50                  55                  60

Lys Thr Ala Asp Ser Gly Tyr Leu Thr Arg Arg Leu
65                  70                  75

<210> SEQ ID NO 58
<211> LENGTH: 87

<212> TYPE: PRT
<213> ORGANISM: Mycoplasma pneumoniae

<400> SEQUENCE: 58

Met Ala Asp Ser Gly Ala Arg Gly Asn Ile Ser Asn Phe Thr Gln Leu
1               5                   10                  15

Phe Gly Met Arg Gly Leu Met Ser Lys Ser Phe Asn Tyr Glu Arg Asn
                20                  25                  30

Asn Gln Ser Lys Ile Ile Lys Asp Thr Ile Glu Val Pro Ile Lys His
            35                  40                  45

Ser Phe Leu Glu Gly Leu Thr Ile Asn Glu Tyr Phe Asn Ser Ser Tyr
        50                  55                  60

Gly Ala Arg Lys Gly Met Thr Asp Thr Ala Met Lys Thr Ala Lys Ser
65                  70                  75                  80

Gly Tyr Met Thr Arg Lys Leu
                85

<210> SEQ ID NO 59
<211> LENGTH: 76
<212> TYPE: PRT
<213> ORGANISM: Bacillus subtilis

<400> SEQUENCE: 59

Met Ala Asp Ser Gly Ala Arg Gly Asn Ala Ser Asn Phe Thr Gln Leu
1               5                   10                  15

Ala Gly Met Arg Gly Leu Met Ala Asn Pro Ala Gly Arg Ile Ile Glu
                20                  25                  30

Leu Pro Ile Lys Ser Ser Phe Arg Glu Gly Leu Thr Val Leu Glu Tyr
            35                  40                  45

Phe Ile Ser Thr His Gly Ala Arg Lys Gly Leu Ala Asp Thr Ala Leu
        50                  55                  60

Lys Thr Ala Asp Ser Gly Tyr Leu Thr Arg Arg Leu
65                  70                  75

<210> SEQ ID NO 60
<211> LENGTH: 76
<212> TYPE: PRT
<213> ORGANISM: Staphylococcus aureus

<400> SEQUENCE: 60

Met Ser Asp Ser Gly Ala Arg Gly Asn Ala Ser Asn Phe Thr Gln Leu
1               5                   10                  15

Ala Gly Met Arg Gly Leu Met Ala Ala Pro Ser Gly Lys Ile Ile Glu
                20                  25                  30

Leu Pro Ile Thr Ser Ser Phe Arg Glu Gly Leu Thr Val Leu Glu Tyr
            35                  40                  45

Phe Ile Ser Thr His Gly Ala Arg Lys Gly Leu Ala Asp Thr Ala Leu
        50                  55                  60

Lys Thr Ala Asp Ser Gly Tyr Leu Thr Arg Arg Leu
65                  70                  75

<210> SEQ ID NO 61
<211> LENGTH: 76
<212> TYPE: PRT
<213> ORGANISM: Mycobacterium tuberculosis

<400> SEQUENCE: 61

Ile Val Asp Ser Gly Ala Thr Gly Asn Phe Thr Gln Thr Arg Thr Leu
1               5                   10                  15

```
Ala Gly Met Lys Gly Leu Val Thr Asn Pro Lys Gly Glu Phe Ile Pro
            20                  25                  30

Arg Pro Val Lys Ser Ser Phe Arg Glu Gly Leu Thr Val Leu Glu Tyr
                35                  40                  45

Phe Ile Asn Thr His Gly Ala Arg Lys Gly Leu Ala Asp Thr Ala Leu
    50                  55                  60

Arg Thr Ala Asp Ser Gly Tyr Leu Thr Arg Arg Leu
65                  70                  75
```

<210> SEQ ID NO 62
<211> LENGTH: 76
<212> TYPE: PRT
<213> ORGANISM: Synechocystis sp.

<400> SEQUENCE: 62

```
Met Ala Phe Ser Gly Ala Arg Gly Asn Met Ser Gln Val Arg Gln Leu
1               5                   10                  15

Val Gly Met Arg Gly Leu Met Ala Asp Pro Gln Gly Glu Ile Ile Asp
            20                  25                  30

Leu Pro Ile Lys Thr Asn Phe Arg Glu Gly Leu Thr Val Thr Glu Tyr
                35                  40                  45

Val Ile Ser Ser Tyr Gly Ala Arg Lys Gly Leu Val Asp Thr Ala Leu
    50                  55                  60

Arg Thr Ala Asp Ser Gly Tyr Leu Thr Arg Arg Leu
65                  70                  75
```

<210> SEQ ID NO 63
<211> LENGTH: 76
<212> TYPE: PRT
<213> ORGANISM: Aquifex aeolicus

<400> SEQUENCE: 63

```
Met Ala Ile Ser Gly Ala Arg Gly Asn Arg Asp Gln Ile Arg Gln Leu
1               5                   10                  15

Ala Gly Met Arg Gly Leu Met Ala Lys His Ser Gly Glu Phe Ile Glu
            20                  25                  30

Thr Pro Ile Ile Ser Asn Phe Arg Glu Gly Leu Ser Val Leu Glu Tyr
                35                  40                  45

Phe Ile Ser Thr Tyr Gly Ala Arg Lys Gly Leu Ala Asp Thr Ala Leu
    50                  55                  60

Lys Thr Ala Phe Ala Gly Tyr Leu Thr Pro Arg Leu
65                  70                  75
```

<210> SEQ ID NO 64
<211> LENGTH: 76
<212> TYPE: PRT
<213> ORGANISM: Deinococcus radiodurans

<400> SEQUENCE: 64

```
Met Ser Gln Ser Gly Ala Arg Gly Asn Pro Gln Gln Ile Arg Gln Leu
1               5                   10                  15

Ala Gly Met Arg Gly Leu Met Ala Arg Pro Asp Gly Ser Thr Ile Glu
            20                  25                  30

Val Pro Ile Arg Ala Ser Phe Arg Glu Gly Leu Thr Val Leu Glu Tyr
                35                  40                  45

Phe Ile Ser Thr His Gly Ala Arg Lys Gly Gly Ala Asp Thr Ala Leu
    50                  55                  60

Arg Thr Ala Asp Ser Gly Tyr Leu Thr Arg Lys Leu
65                  70                  75
```

<210> SEQ ID NO 65
<211> LENGTH: 76
<212> TYPE: PRT
<213> ORGANISM: Thermus thermophilus

<400> SEQUENCE: 65

```
Met Ala Gln Ser Gly Ala Arg Gly Asn Pro Gln Gln Ile Arg Gln Leu
1               5                   10                  15

Cys Gly Leu Arg Gly Leu Met Asp Lys Pro Ser Gly Glu Thr Phe Glu
            20                  25                  30

Val Pro Val Arg Ser Ser Phe Arg Glu Gly Leu Thr Val Leu Glu Tyr
        35                  40                  45

Phe Ile Ser Ser His Gly Ala Arg Lys Gly Gly Ala Asp Thr Ala Leu
    50                  55                  60

Arg Thr Ala Asp Ser Gly Tyr Leu Thr Arg Lys Leu
65                  70                  75
```

<210> SEQ ID NO 66
<211> LENGTH: 76
<212> TYPE: PRT
<213> ORGANISM: Thermus aquaticus

<400> SEQUENCE: 66

```
Met Ala Gln Ser Gly Ala Arg Gly Asn Pro Gln Gln Ile Arg Gln Leu
1               5                   10                  15

Cys Gly Met Arg Gly Leu Met Asp Lys Pro Ser Gly Glu Thr Phe Glu
            20                  25                  30

Val Pro Val Arg Ser Ser Phe Arg Glu Gly Leu Thr Val Leu Glu Tyr
        35                  40                  45

Phe Ile Ser Ser His Gly Ala Arg Lys Gly Gly Ala Asp Thr Ala Leu
    50                  55                  60

Arg Thr Ala Asp Ser Gly Tyr Leu Thr Arg Lys Leu
65                  70                  75
```

<210> SEQ ID NO 67
<211> LENGTH: 96
<212> TYPE: PRT
<213> ORGANISM: Homo sapiens

<400> SEQUENCE: 67

```
Met Val Gln Ser Gly Ala Lys Gly Ser Thr Val Asn Thr Met Gln Ile
1               5                   10                  15

Ser Cys Leu Leu Gly Gln Ile Glu Leu Glu Gly Arg Ser Thr Pro Leu
            20                  25                  30

Met Ala Ser Gly Lys Ser Leu Pro Cys Phe Glu Pro Tyr Glu Phe Thr
            35                  40                  45

Pro Arg Ala Gly Gly Phe Val Thr Gly Arg Phe Leu Thr Gly Ile Lys
    50                  55                  60

Pro Pro Glu Phe Phe Phe His Cys Met Ala Gly Arg Glu Gly Leu Val
65                  70                  75                  80

Asp Thr Ala Val Lys Thr Ser Arg Ser Gly Tyr Leu Gln Arg Cys Ile
                85                  90                  95
```

<210> SEQ ID NO 68
<211> LENGTH: 96
<212> TYPE: PRT
<213> ORGANISM: Homo sapiens

<400> SEQUENCE: 68

```
Met Val Val Ser Gly Ala Lys Gly Ser Lys Ile Asn Ile Ser Gln Val
1               5                   10                  15

Ile Ala Val Val Gly Gln Gln Asn Val Glu Gly Lys Arg Ile Pro Phe
                20                  25                  30

Gly Phe Lys His Arg Thr Leu Pro His Phe Ile Lys Asp Asp Tyr Gly
            35                  40                  45

Pro Glu Ser Arg Gly Phe Val Glu Asn Ser Tyr Leu Ala Gly Leu Thr
        50                  55                  60

Pro Thr Glu Phe Phe Phe His Ala Met Gly Gly Pro Glu Gly Leu Ile
65                  70                  75                  80

Asp Thr Ala Val Lys Thr Ala Glu Thr Gly Tyr Leu Gln Arg Arg Leu
                85                  90                  95

<210> SEQ ID NO 69
<211> LENGTH: 96
<212> TYPE: PRT
<213> ORGANISM: Homo sapiens

<400> SEQUENCE: 69

Met Ala Leu Cys Gly Ser Lys Gly Ser Phe Ile Asn Ile Ser Gln Met
1               5                   10                  15

Ile Ala Cys Val Gly Gln Gln Ala Ile Ser Gly Ser Arg Val Pro Asp
                20                  25                  30

Gly Phe Glu Asn Arg Ser Leu Pro His Phe Glu Lys His Ser Lys Leu
            35                  40                  45

Pro Ala Ala Lys Gly Phe Val Ala Asn Ser Phe Tyr Ser Gly Leu Thr
        50                  55                  60

Pro Thr Glu Phe Phe Phe His Thr Met Ala Gly Pro Glu Gly Leu Val
65                  70                  75                  80

Asp Thr Ala Val Lys Thr Ala Glu Thr Gly Tyr Met Gln Arg Arg Leu
                85                  90                  95
```